United States Patent [19]
Kozhemyakin et al.

[11] Patent Number: 6,165,979
[45] Date of Patent: *Dec. 26, 2000

[54] CYTOKINE AND HEMOPOIETIC FACTOR ENDOGENOUS PRODUCTION ENHANCER AND METHODS OF USE THEREOF

[75] Inventors: Leonid A. Kozhemyakin; Mark B. Balazovski, both of St. Petersburg, Russian Federation

[73] Assignee: Novelos Therapeutics, Inc., Newton, Mass.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/733,886

[22] Filed: Oct. 18, 1996

[30] Foreign Application Priority Data

Dec. 14, 1995 [RU] Russian Federation .............. 95120403
May 21, 1996 [RU] Russian Federation .............. 95120403

[51] Int. Cl.$^7$ .......................... A61K 38/06; A61K 38/08
[52] U.S. Cl. ................................................ 514/17; 514/18
[58] Field of Search ...................... 514/17, 18, 6; 530/331, 332

[56] References Cited

U.S. PATENT DOCUMENTS

| | | | |
|---|---|---|---|
| 4,761,399 | 8/1988 | Pilotto et al. ............................. | 514/19 |
| 4,871,528 | 10/1989 | Tognella et al. ......................... | 434/649 |
| 4,927,808 | 5/1990 | Kitahara et al. .......................... | 514/19 |
| 4,968,671 | 11/1990 | Asano et al. .............................. | 514/18 |
| 5,248,697 | 9/1993 | Wilmore .................................... | 514/563 |
| 5,916,878 | 6/1999 | Kolobov et al. ........................... | 514/19 |

FOREIGN PATENT DOCUMENTS

| | | |
|---|---|---|
| 0502313 | 9/1992 | European Pat. Off. . |
| 616 803 A2 | 2/1994 | European Pat. Off. . |
| 4-9336 | 1/1992 | Japan . |
| WO 94/00141 | 1/1994 | WIPO . |
| WO94/00141 | 6/1994 | WIPO . |
| WO 96/40205 | 12/1996 | WIPO . |

OTHER PUBLICATIONS

Araie, M., et al. (1988) Invest. Ophthalmal. Vis. Sci. 29: 1884–87.
Krieter, H., et al. (1994) Cardiosci. 5: 115–26.
Hansson M., Soderstrom T. The colony stimulating factors. Med Oncol Tumor Pharmacother. 1993. 10(1–2), p. 5–12.
Dillman R.O. The clinical experience with interleukin–2 in cancer therapy. Cancer Biother. 1994 Fal. 9(3). p. 183–209.
Hieber U., Heim M E. Tumor necrosis factor for the treatment of malignancies. Oncology. 1994 Mar–Apr. 51(2) p. 142–53.
Neidhart J.A. Hematopoietic cytokines. Current use in cancer therapy. Cancer. 1993 Dec. 1. 72 (11 Suppl)., p. 3381–6.
Murray H.W. Interferon–gamma and host antimicrobial defense: current and future clinical applications. Am J Med. 1994 Nov. 97(5), p. 459–67.
Cirelli R. Tyring S. K. Interferons in human papillomavirus infections. Antiviral Res. 1994 Jul. 24(2–3), p. 191–204.
Sher A. Coffman R.L. Regulation of immunity to parasites by T–cells and T–cell derived cytokines. Annu. Rev. Immunol., 1992. 10. p. 385–409.
Offenstadt G., Guidet B., Staikowsky F. Cytokines and severe infections. Pathol Biol. (Paris). Oct. 1993 41 (8 Pt 2). p. 820–31.

(List continued on next page.)

Primary Examiner—Jeffrey E. Russel
Attorney, Agent, or Firm—Wolf, Greenfield & Sacks, P.C.

[57] ABSTRACT

A method of stimulating endogenous production of cytokines and hemopoietic factors by introducing to a mammalian body in need of stimulation of cytokines or hemopoietic factors or both, an effective amount of oxidized glutathione, for a period of time to stimulate said endogenous production to obtain a therapeutic effect. Oxidized glutathione with or without extenders are used in drug forms.

33 Claims, 2 Drawing Sheets

Glutathione oxidized (GSSG)

OTHER PUBLICATIONS

Nelson S. Role of granulocyte colony–stimulating factor in the immune response to acute bacterial infection in the nonneutropenic host: an overview. Clin Infect Dis. 1994 Feb. 18, 1994 Suppl 2P S197–204.

Nemunaitis J Use of hematopoietic growth factors in marrow transplantation Curr Opin Oncol Mar. 1994, 6(2). p. 139–45.

Forman A.D. Neurologic complications of cytokine therapy. Oncology (Huntingt). 1994 Apr. 8(4), p. 105–10: discussion 113. 116–7.

Mittelman M., Lessin L. S. Clinical application of recombinant erythropoietin in myelodysplasia. Hematol Clin North Am. 1994 Oct. 8(5), p. 993–1009.

Hack C.E., Ogilvie A.C., Eisele B., Eerenberg A.J., Wagstaff J., Thijs L.G. C1–inhibitor substitution therapy in septic shock and in the vascular leak syndrome induced by high doses of interleukin–2. Intensive Care Med. 1993. 19 Suppl 1P S19–28.

Saito M. OK–432, a killed streptococcal preparation, in the treatment of animal and human cancer and its mechanisms of action. Form on i mmunomodulators. Ed. Guenounou M. John Libbey Eurotext. Paris. 1995. p. 1–11, Barot–Ciorbaru R., Bona C. Immunomodulators from *Nocardia opaca* Form on immunomodulators. Ed. Guenounou M. John Libbey Eurotext. Paris, 1995. p. 1–11.

Meister A. Anderson M.E. Glutathione. Annu. Rev. Biochem., 1983. 52:711–60.

Beutler E. Nutritional and metabolic aspects of glutathione. Review. Annu. Rev. Nutr., 1989, 9:287.

Textbook of biochemistry: with clinical correlations, Ed. Devlin T.M., 3rd ed. 1992. Wiley–Liss, N.Y. p. 525.

Ehrer J.P., Lund L.G. Cellular reducing equivalents and oxidative strees. Free Radic Biol Med. 1994 Jul. p. 65–75.

Michiels C., Raes M., Toussaint Ol, Remacle J. Importance of Se–glutathione peroxidase, catalase. and Cu/Zn–SOD for cell survival against oxidative stress. Free Radic Biol Med. 1994 Sep. 17(3), p. 235.48.

Cohen G. Enzymatic/nonenzymatic sources of oxyradicals and regulation of antioxidant defenses. Ann NY Acad Sci. 1994 Nov. 17, 738, p. 8–14.

Beckett G.J., Hayes J.D. Glutathione S–transferase: biomedical applications. Advan. Clin. Chem. 1993 vol. 30, p. 281–380.

Droge W., Schultze–Osthoff K., Mihm S., Galter D., Schenk H., Eck H.P., Roth S., Gmunder H. Functions of glutathione and glutathione disulfide in immunology and immunopathology, FASEB J. Nov. 8, 1994 (14) p. 1131–8.

Giugliano D., Ceriello A., Paoliso G. Diabetes mellitus, hypertension, and cardiovascular disease; which role oxidative stress? Metabolism, Mar. 1995 44(3), p. 363–8.

Keusch G.T. Antioxidants in infection, J Nutr Sci Vitaminol (Tokyo), 1993, 39 Suppl P S 23–33.

Sokolovsky M., Wilchek M. Patchornik A. On the synthesis of cystein peptides, J. Amer. Chem. Soc. 1964, Mar. 86(6), p. 1202–6.

Glutathione oxidized (GSSG)

CYTOKINE AND HEMOPOIETIC FACTOR ENDOGENOUS PRODUCTION ENHANCER AND METHODS OF USE THEREOF

FIELD OF THE INVENTION

The present invention relates to medicine and more particularly to pharmacology and therapy, and is intended to be used for preventing and treating various diseases by way of increasing endogenous production of cytokines and hemopoietic factors.

BACKGROUND OF THE INVENTION

It has been known that a number of endogenously produced mammalian humoral factors, i.e. cytokines and hemopoietic factors possess important biological activities that are considerably helpful in treating various human diseases[1,2]. Many of these factors are being tested in man, those with proven efficiency being commercially available as medicinal agents.

The following cytokines and hemopoietic factors are being most extensively researched in oncology: interleukin 2 (IL-2)[3,4], tumor necrosis factor alpha (TNF-α)[5], erythropoietin, macrophage-granulocyte and granulocyte colony-stimulating factors (GM-CSF and G-CSF, respectively[6,7]). No less actively is being studied the use of cytokines and hemopoietic factors for the treatment of infectious disease: interferons (IFN-γ and IFN-β)[8,9,10], colony-stimulating factors[11,12], and the like[13]. Colony-stimulating factors and erythropoietin are broadly used in hematology[14,15].

However, the medicinal use of these exogenously administered agents has its limitations associated with the lack of acceptable drug formulations or their exorbitant cost, a short half-life of these substances in biological media, difficulties in dose finding as well as numerous toxic and allergic effects[16,17], since even the recombinant products are more or less immunogenic to the human organism because of the processing fluctuations in the course of the artificial synthesis.

In this regard, in view of achieving a more invariable and significant therapeutic effect free of adverse reactions, it is preferable to induce the endogenous production of the autologous cytokines and hemopoietic factors immediately within the organism of a subject. The remedial effect due to such intrinsic stimulation is free of all the disadvantages associated with exogenously introduced cytokines and hemopoietic factors.

A number of compounds are currently being evaluated that stimulate endogenous production of cytokines and hemopoietic factors in both experimental and clinical settings. There are universally known cases, including successful ones, of using microbial products for cancer therapy which in recent decades has been shown to be mediated via stimulation of the tumor necrosis factor endogenous production[18]. The products capable of evoking concomitant production of various cytokines and hemopoietic factors have presently come to be known as multi-cytokine inducers. Among these are a killed streptococcal preparation, Nocardia Opaca, and other bacterial products[19,20,21]. However, virtually all the substances possessing such capability are either killed microorganisms or microbial products or compounds having irregular composition, which results in their limited medicinal utility or even renders their therapeutic use impracticable. Thus, the problem of finding a medically and pharmaceutically acceptable inducer of the cytokine and hemopoietic factor endogenous production has not heretofore been resolved.

Oxidized glutathione (also known as glutathione disulfide and GSSG) will often be referred to as GSSG in this application.

GSSG is known as a dimmer of tripeptide glutathione (γ-glutamyl-cysteinyl-glycine) where two molecules of the tripeptide with the above structure are linked via a covalent disulfide bond between the cystamine residues. Therefore, both the tripeptide glutathione (glutathione, reduced glutathione, GSH; hereinafter referred to as GSH) and its dimmer GSSG are natural metabolites present in animal tissues and biological fluids. At the same time, the natural blood level of GSSG is not sufficient for inducing the cytokine endogenous production in both normal and pathological conditions.

GSH is known to be one of the most important intermediates in the amino acid metabolism and a factor maintaining the intracellular homeostasis[22,23]. The reducing properties of GSH and its function as a donor of reduction equivalents, which is due to the sulfhydryl moiety of the cystamine residue, are of key importance. This characteristic of GSH is responsible for the substance playing a crucial part in one of the most important intracellular antioxidant systems, consisting of GSH as such and two enzymes of its reversible conversion into GSSG: glutathione peroxidase and glutathione reductase[24,25]. The permanent functioning of said system is essential for inactivating or reducing endogenously generated oxidants as well as active metabolites of foreign substances[26,27].

GSH is also known to participate in detoxification reactions involving a group of enzymes collectively known as glutathione S-transferase[28]. These enzymes are capable of conjugating the GSH molecule with various xenobiotics by forming a bond between the latter and glutathione via the thiol moiety of the cystamine residue of the tripeptide. The subsequent degradation of the conjugate is catalyzed by the γ-glutamyl cycle enzymes, and may vary considerably depending upon the nature of the xenobiotic.

Under natural conditions, GSSG does not accumulate in amounts sufficient for inducing cytokine and hemopoietic factor production, due to a constant reduction of GSSG to GSH. The GSSG reduction to GSH also actively progresses in the intestines and liver upon GSSG oral administration, and as any product made of amino acids, the substance is proteolytically degradable in the gastrointestinal tract.

GSSG is known to be used as a components of a nutritional supplement utilized as an adjunct diet in treating patients[29]. However, being a peptide substance, most of the orally administered GSSG is digested in the gastrointestinal tract with the remainder being reduced in the intestinal and hepatic cells to GSH and not entering the circulation. Therefore, the delivery of GSSG into the organism through the gastrointestinal tract may eliminate the possibility of the realization of its activity as a stimulator of endogenous production of cytokines and hemopoietic factors.

An elevation of the GSH endogenous levels for medicinal utility is known to be suggested for boosting immunity[30] and treating toxemias, poisonings, diabetes, mellitus, cardiovascular, infectious and other disorders[31,32,33]. Possible functions of GSH and GSSG appear in the literature.

Exogenous GSH or its direct (γ-glutamyl-cystamine, n-acetyl-cystamine, and n-acetyl-cystamine-glycine) or indirect (2-oxothiazolidine-4-carboxylate) biochemical precursors, or their salts and esters, are reportedly used as medicinal agents and dietary supplements in treating various disease[34,35,36,37,38].

GSH is also claimed to be useful as a chemoprotective agent that prevents neurotoxicity in cancer chemotherapy[39]

as well as in combination with antineoplastics in order to augment their effect[40].

No reference, however, is currently available to GSSG as a medicine in its own right (sole substance) used to induce the endogenous production of cytokines and hemopoietic factors. The substance is known neither to have medicinal effects in human and animal diseases nor to be applied as a pharmaceutical agent for treating illnesses.

SUMMARY OF THE INVENTION

It is an object of the present invention to provide an active substance, and advantageous combinations of said substance and extenders, capable of inducing endogenous cytokine and hemopoietic factor production to an individual or a subject in need thereof.

"Subject in need thereof" as used in this application is intended to mean a mammal, e.g., man, domestic animals and livestock including cats, dogs, cattle and horses, having one or more manifestations of a disease in which stimulation of endogenous cytokine or hemopoietic factor (or both) production would be considered beneficial by those skilled in the art. "Therapeutic agent" as used in this application is meant to include any drug form of GSSG-containing material or GSSG alone, which has a therapeutic effect on neoplastic, infectious, hematologic, immunologic or other diseases. Therapeutic effect, as will be further defined, indicates any effect in man and other mammals which is beneficial, including curative, preventative, allowing maintenance at a beneficial level, or is in any way advantageous in connection with the body of man and other mammals.

In accordance with the present invention, it is GSSG that upon parenteral administration induces the endogenous cytokine and/or hematopoietic factor production in an individual or subject in need thereof, in both health and disease.

Having performed studies in search for a medically and pharmaceutically acceptable inducer of the cytokine and hemopoietic factor endogenous production, the applicants discovered a new property of a previously known substance, oxidized glutathione (oxidized glutathione, glutathione disulfide, GSSG; hereinafter often referred to as GSSG).

Being administered parenterally or acting on isolated cells, the substance is capable of inducing production of several cytokines and hemopoietic factors in mammals (animals and humans) in both health and disease.

The inducer or stimulator of the endogenous cytokine and hemopoietic factor production is oxidized glutathione (GSSG) which is a dimmer of reduced glutathione having the structure γ-glutamyl-cysteinyl-glycine, where the two molecules of the tripeptide are linked via a covalent disulfide bond between the cystamine residues.

According to the invention, a method is provided for stimulating endogenous production of cytokine and hemopoietic factors by introducing to a mammalian body in need of stimulation of cytokine or hemopoietic factor or both, an effective amount of oxidized glutathione for a period of time to stimulate said endogenous production to obtain a therapeutic effect.

Preferably, the glutathione is introduced parenterally or topically. In a preferred form, the method is carried out by introducing the oxidized glutathione (GSSG) with an extender of half life to enhance the desired effect of stimulating endogenous production and producing a therapeutic effect in a body.

Preferably, the extender is selected from the group consisting of pro-oxidant compounds, materials which are competitors of NADP.H-dependent reduction of GSSG into GSH catalyzed by glutathione reductase, compounds capable of producing reversible inhibition of reduction of NADP+ into NADP.H catalyzed by glucose-6-phosphate-dehydrogenase or by other NADP+-dependent enzymes, or mixtures thereof.

Particularly desirable extenders are hydrogen peroxide, inosine or cystamine or mixtures thereof.

In the preferred form, GSSG is introduced to the body at a dose of from 0.1 to 0.5 mg per kg of body weight at least one time during each 24 hour period, although it can be continuously injected or otherwise introduced to the body to have a 24 hour total dosage of from 0.1 to 0.5 mg per kg of body weight each 24 hour period. Preferably, administration and introduction to the body is carried out until a desired stimulating effect increasing production and providing a therapeutic effect is obtained.

According to the invention, a therapeutic agent for treating neoplastic, infectious, hematologic, immunologic and other diseases is provided, comprising an effective amount of oxidized glutathione, along with a pharmaceutically acceptable excipient. Preferably, the oxidized glutathione for parenteral use is in a pharmaceutically acceptable solvent as, for example, an aqueous solution including water, glucose solution, isotonic solutions of sodium chloride, buffered salt solutions. Preferably a pharmaceutically acceptable extender capable of enhancing and prolonging therapeutic effect as by increasing the half life of oxidized glutathione is used along with the GSSG.

The applicant has for the first time shown that an immediate action of exogenous GSSG on mammalian (human and laboratory animal) cells capable of producing cytokines and hemopoietic factors, exerts stimulation on the synthesis of these molecules and their increased level in the blood serum (in vivo conditions) or culture media (in vivo and ex vivo or in vitro conditions). The method suggested can bring about the effect of stimulating production of cytokines and hemopoietic factors, and this effect is elicited by the administration of GSSG into the organism or entering into the cultural media, as well as by the administration of GSSG in combination with pharmacologically active formulations mediating the prolongation of glutathione's retaining the oxidized form. The studies performed by the applicant have revealed GSSG and its formulations to possess a therapeutic effect in various experimental and clinical pathological conditions.

The revealed GSSG-induced stimulation of the endogenous cytokine and hemopoietic factor production in the body results in antitumor, anti-infective, hemopoietic, immunomodulatory and other pharmacological effects resulting, in turn, to a greater or lesser extent therapeutic or preventive effect in various diseases.

BRIEF DESCRIPTION OF THE DRAWINGS

The above and other objects, features and advantages of the present invention will be better understood from the following specification when read in connection with the accompanying drawing in which.

DESCRIPTION OF PREFERRED EMBODIMENTS

In accordance with the present invention, the medicinal agent suggested for treating neoplastic, infectious, hematologic, and other diseases, in which stimulation of the endogenous cytokine and hemopoietic factor production is appropriate, has an effective amount of GSSG as its active principle. It is also advantageous to prepare a drug form of the medicinal agent as an injectable solution containing 0.01 to 2.0% GSSG.

Figure 2:
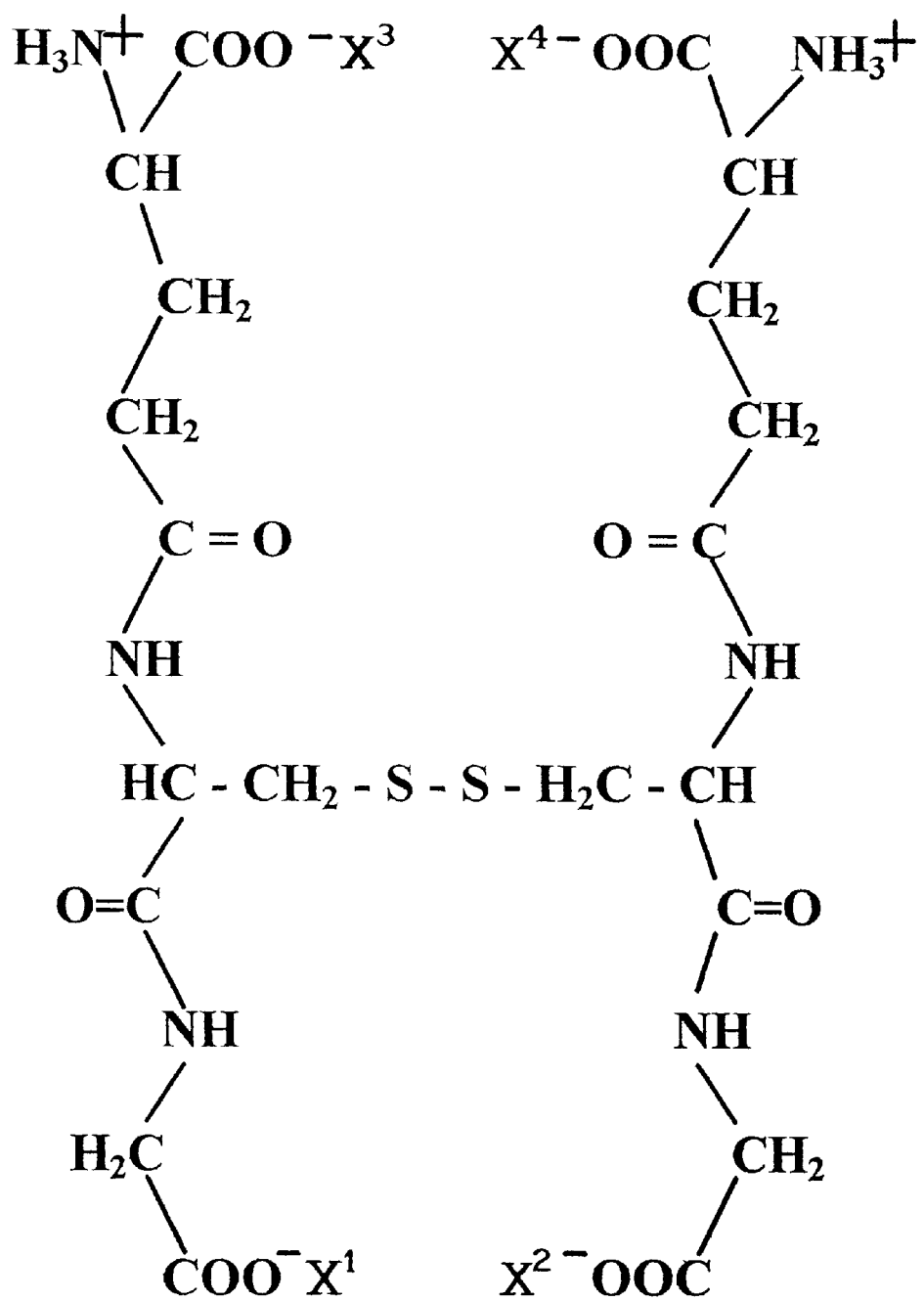
FIG. 2 is a drawing of GSSG structure.

The GSSG used as a therapeutic or medicinal agent in accordance with the present invention is shown in FIG. 2. GSSG is preferably used in a carrier or solution as, for example, isotonic solution of sodium chloride, glucose solution, other buffer and salt solutions. Any aqueous based or solvent based carrier or solvent can be used as long as the overall solution or dispersion is compatible with the body and pharmaceutically acceptable i.e., it does not cause any unwanted side effects in the body or unwanted interaction with GSSG.

In the structural formula of FIG. 2, points X1, X2, X3 and X4 are noted as sites for chemical modification of the GSSG. Generally, the GSSG is used in the form shown in solution or can be any of its physiologically acceptable soluble salts. The disodium salt where X1, X2, are sodium ions are preferred for best solubility of the drug and optimum transfer characteristics across cell membranes into the cells. X1, X2, X3 and X4 can each be hydrogen if other substitutes are not used. Other salts of GSSG can be used, so long as they are pharmaceutically acceptable, i.e., do not adversely affect the body, for example, X1, X2, X3 and X4 can all be (or one or more of them can be) potassium or calcium. Water soluble salts are preferred for use in this invention.

In accordance with the present invention, it is expedient to use such GSSG drug forms and/or pharmaceutical compositions that prolong oxidized glutathione half-life in tissues and biological fluids, or augment the revealed biological and therapeutic properties of GSSG.

In accordance with the present invention, with the purpose of augmenting and prolonging the therapeutic effect of GSSG, its drug form (injectable solution) is suggested to contain a pharmaceutically acceptable component or extender, capable of extending or enhancing the oxidized glutathione half-life.

As a pharmaceutical acceptable component or extender to prolong glutathione permanence in oxidized form, 0.003% hydrogen peroxide can be offered for application. This is because in the presence of hydrogen peroxide, a donor of reactive oxygen intermediates (that is an oxidant), GSSG is reduced by glutathione reductase to GSH at a lesser speed, thereby conditioning a slower reduction of GSSG introduced exogenously into biological media. Hydrogen peroxide preferably can be used in amounts of from 0.03 to 0.0003% by weight of solutions used Usage of an acceptable concentration of hydrogen peroxide ($H_2O_2$) in formulation of the drug form for parenteral administration, as well as usage of any other prooxidant compounds (donors of active oxygen form), makes it possible to realize only one of possible methods of the prolongation of oxidized glutathione half-life in the biological fluids and tissues and, thereby, to enhance and prolong the pharmaceutical effect of GSSG.

We have also found some other pharmaceutically acceptable components or extenders capable of mediating the slowdown of the reduction of exogenous GSSG into GSH in biological media. Such, in particular, are the factors capable of setting up competitive relations with a reduced form of the nicotinamide adenine dinucleotide phosphate or NADP.H, for example, inosine (and other derivatives of hypoxanthine), as well as the agents reversibly inhibiting the processes of reduction of the oxidized form of NADP+ into NADP.H, for example, cystamine (2,2'-Dithio-bis [ethylamine]) and other inhibitors of glucose-6-phosphate-dehydrogenase.

Since reduced. NADP.H is the key cofactor of glutathione reductase system catalyzing the reduction of GSSG into GSH, any pharmaceutically acceptable compounds or biophysical influence retarding the reduction of GSSG or blocking biological oxidation of NADP.H by glutathione reductase will facilitate preservation of GSSG from reduction in biological media and, therefore, will enhance and prolong its curative effect.

Due to conducted research we were the first to discover that GSSG pharmaceutical and medicinal effect will reinforce, when GSSG used in combination with agents capable of competition with NADP.H, as well as with compounds reversibly inhibiting the enzymatic reaction, catalyzed by glucose-6-phosphate-dehydrogenase which mediates the reduction of the oxidized form of NADP+. Reversible inhibitors or pentose phosphate pathway of glucose oxidation can be used.

Thus, besides hydrogen peroxide, one of other pharmacologically accepted components capable to prolong the oxidized glutathione half-life can be inosine (hypoxanthine-9-D-ribofuranoside) used most preferably as 0.1% solution and preferably as a solution of from 0.1% to 5% by weight.

The investigations carried out showed inosine to facilitate biological and therapeutical effects of GSSG. It was demonstrated that this property of inosine is based on its ability to compete with NADP.H, and thereby, to retard GSSG reduction into GSH. Moreover, we have also found that other hypoxanthine derivatives (including inosine, nucleoside ones, hypoxanthine riboside and other nucleoside derivatives of inosine) possess this property as well.

Also, besides hydrogen peroxide and inosine, cystamine (2,2'-Dithio-bis[ethylamine]) is another pharmaceutically acceptable agent conditioning a slower reduction of GSSG, if used most preferably as 0.1% solution and preferably as a solution of from 0.1% to 3% by weight.

Our research showed cystamine to facilitate biological and therapeutical effects of GSSG. The effect is due to the cystamine ability to act as a reversible inhibitor of key enzyme of the pentose phosphate pathway, glucose-6-phosphate-dehydrogenase, mediating reduction of NADP+ into NADP.H.

Thus, the present invention suggests the method to enhance the ability of GSSG to stimulate endogenous production of cytokines and hemopoietic factor which presupposes the usage a pharmaceutical composition including GSSG and an additional component able to prolong the oxidized glutathione half-life. This can be achieved by the administration of pharmaceutically acceptable compositions including drug forms of GSSG and drug forms of other products, able to prolong the oxidized glutathione half-life, such as: 0.003% hydrogen peroxide or other compounds with oxidant activity; 0.1% inosine (hypoxanthine-9-D-ribofuranoside) or its derivatives including inosine nucleosides; and also 0.1% cystamine (2,2'-Ditio-bis[ethylamine]) or other compounds, capable to produce reversible inhibition of glucose-6-phosphate-dehydrogenase, the key enzyme of the pentose phosphate pathway.

It is found that the parenteral (intravenous, intraperitoneal, intramuscular, etc.) administration of GSSG in 0.003% solution of hydrogen peroxide, or GSSG in 0.1% inosine solution, or GSSG in 0.1% cystamine solution stimulates endogenous production or TNF-α, IFN-α and IFN-γ, IFN-B, IL-IB, IL-1, IL-2, IL-6, IL-10, G-CSF, colony stimulating factors, erythropoietin, and GM-CSF in organism of experimental animals in a larger degree than with the application of GSSG alone.

The studies carried out prove the ability of the above mentioned compounds to enhance the biological and therapeutical effects of GSSG, which makes evident the expediency of their use in combination with GSSG to treat neoplastic, infectious, hematological and other diseases in which stimulation of the endogenous cytokine and hemopoietic factor production is considered beneficial by those skilled in the art.

Thus, in accordance with the present invention, for the purpose of enhancing and prolonging the GSSG therapeutical effect, it is preferred that a final drug formulation (1–5 ml of solution for injections) should contain additional pharmaceutically acceptable components able to prolong the oxidized glutathione half-life in the biological media. They can be the following:

a) 0.003% hydrogen peroxide or any other pharmaceutically acceptable pro-oxidant compounds with activity of the donors of reactive oxygen intermediates;

b) 0.1% inosine (hypoxanthine-9-ribofuranoside) or any other pharmaceutically acceptable competitors of NADP.H-dependent reduction of GSSG into GSH catalyzed by glutathione reductase;

c) 0.1% cystamine (2,2'-Dithio-bis[ethylamine]) or any other pharmaceutically acceptable compounds able to produce reversible inhibition or reduction of NADP+ into NADP.H catalyzed by glucose-6-phosphate-dehydrogenase or by other NADP.H-dependent enzymes.

At the same time, the data were obtained to testify the direct antitumor effect of GSSG, or GSSG administered together with the pharmaceutically acceptable compounds prolonging oxidized glutathione half-life in biological media. Moreover, the GSSG effect was proved to be different for normal and tumor cells. Our in vitro research with the use of normal and tumor cells revealed that the GSSG alone, or its pharmaceutically acceptable compositions containing compounds prolonging oxidized glutathione half-life in biological media, initiated tumor cell death in apoptosis like manner. In case of normal cells, they did not undergo destruction.

It is an object of the present invention to provide a method for treating neoplastic, infectious, hematologic and other diseases in which stimulation of the endogenous cytokine and hemopoietic factor production is advantageous. The method comprises parenteral administration of GSSG as the medicinal agent in the injectable drug form at 0.01 to 0.5 mg GSSG per kg body weight, one or more times a day, by one or more day pulses or continuously until a desired therapeutic effect has been achieved. It is essential that either GSSG as medicinal agent or its drug forms and/or pharmaceutical compositions be administered strictly parenterally so that to prevent or minimize its deregulation or reduction (to GSH) taking place in the gastrointestinal tract upon oral administration. However, the GSSH with or without enhancers can be applied topically to the body at a dose consistent with the parenteral dose as for example 0.01 to 0.5 mg GSSG per meter$^2$ of skin or topical areas of the body being treated.

Provided the GSSG molecule is protected from proteolysis and/or reduction to GSG, it would be advantageous to administer the agent orally and/or intralesionally (in situ) (wound, tumor, etc.).

The examples given below confirm that the parenteral (intraperitoneal, intravenous, intramuscular, subcutaneous, etc.) use of GSSG results in inducing the endogenous production of inter alia TNF-α, IFN-α and IFN-γ, IL-1, IL-2, IL-6, IL-10, erythropoietin, and GM-CSF in mammals, which elicits a significant therapeutic effect in animals and humans suffering from neoplastic or infectious disease, hemopoiesis and immunity suppression of different origin, and other diseases in which stimulation of the endogenous cytokine and hemopoietic factor production would be considered beneficial by those skilled in the art.

From the experimental findings (see Examples) it follows that the previously unknown GSSG capability of inducing the endogenous cytokine and hemopoietic factor production and exerting beneficial effects in various diseases, is not associated with an increase in GSH levels, because GSH testing in a wide range of doses and concentrations has revealed neither stimulation of the endogenous cytokine and hemopoietic factor production nor the therapeutic effect observed with the use of GSSG.

GSSG can be used along with other medicaments without causing unwanted interaction in the body. For example, patients treated with known drugs such as lithium, ibuprofen, aminophylline, antibiotics, AZT, calcium antagonists, tamoxifen, hormones, interferon, and others can be treated simultaneously with GSSG.

As used herein, the term "therapeutic effect" means any improvement in the condition of a patient or animal treated according to the subject method, including obtaining a preventative or prophylactic effect, or any alleviation of the severity of signs and symptoms of a disease and its sequelae, including those caused by other treatment methods (e.g., chemo- and X-ray therapy), which can be detected by means of physical examination, laboratory or instrumental methods and considered statistically and/or clinically significant by those skilled in the art.

As used herein, the term "prophylactic effect" means prevention of any worsening in the condition of a subject treated according to the method of the invention, as well as prevention of any exacerbation of the severity of signs and symptoms of a disease or its sequelae, including those caused by other treatment methods (e.g. chemo- and X-ray therapy), which can be detected by means of physical examination, laboratory or instrumental methods and considered statistically and/or clinically significant by those skilled in the art.

As used herein, the terms "neoplastic and infectious disease", "hemopoiesis and immunity depression of various origin", and "other diseases" mean any neoplastic and infectious disease, any condition caused or accompanied by the erythroid or myeloid suppression, or a reduction in quantitative or functional immunity parameters, as well as any other disease or pathological condition in which stimulation of the endogenous cytokine and/or hemopoietic factors including but not limited to TNF-α, IFN-α, and INF-γ, IL-1, IL-2, IL-6, IL-10, erythropoietin, and GM-CSF, production would be considered advantageous by those skilled in the art.

The non-limiting examples given below demonstrate feasibility of the invention.

The active principle, the GSSG peptide capable of inducing the endogenous cytokine and hemopoietic factor production, may be obtained by conventional peptide synthesis techniques[41].

Thereby obtained peptide (GSSG) is subsequently used in animals and humans (in vivo) as the GSSG base, or as a pharmaceutically acceptable GSSG salt, in an injectable drug form prepared by dissolving the bulk substance in injectable water, or in any pharmaceutically acceptable solvent, with the resultant concentration of the active compound being 0.01–2.0% by weight.

For an in vitro use in experimental settings, GSSG may be dissolved in biologically acceptable solvents such as culture media, isotonic saline solutions, glucose solutions and the like. Preferably an aqueous carrier or solvent is used, although and physiological and other solvents or carrier can be used. For topical application, organic solvents or carriers may be used in the form of ointments, pastes, creams or suppositories for body orifice applications.

The drug form for human and animal use should be prepared under sterile and pyrogen-free conditions while exerting every effort to prevent chemical or bacterial contamination, thereby providing a sterile, pyrogen free treating agent or drug form.

The GSSG injectable drug form has been tested in both animal studies and pilot human trials.

The use of the maximum achievable concentration of the GSSG sodium salt solution (10.0%, 100 mg/mL) in injectable water (or in normal saline, or in 0.003% hydrogen peroxide, or in 0.1% cystamine), and the maximum tolerable volumes administered to mice intraperitoneally (IP<2.0 mL), intravenously (IV, 0.5 mL), and intramuscularly (IM, 0.05 mL), have made it feasible to reach GSSG dosage levels 5000 mg/kg (IP), 1350 mg/kg (IV), and 135 mg/kg (IM), i.e. 1000, 270, and 27 times, respectively, the maximum recommended human dose of 0.5 mg/kg. In none of the cases either animals' deaths or any toxic signs were observed, showing GSSG in injectable drug form to be essentially non-toxic.

The results of nonclinical evaluation of biological, pharmacological, and therapeutic properties of GSSG, we well as its drug forms with or without 0.003% hydrogen peroxide, or 0.1% inosine, or 0.1% cystamine, are presented in Examples ##1–5.

EXAMPLE #1

Effect of GSSG and Its Drug Forms on Cytokine Production by Human Peripheral Blood Mononuclear Leukocytes In Vitro Oxidized glutathione (GSSG), as well as its drug forms containing 0.003% hydrogen peroxide, or 0.1% inosine, or 0.1% cystamine, were evaluated for their effect on cytokine production by human peripheral blood mononuclear leukocytes in vitro.

The leukocytic cytokine production was triggered by adding a mitogen, concanavalin A (ConA) to the cell culture immediately after introducing the test substances. In 24 hours of the cellular exposure to ConA and the test articles, the culture supernatants were sampled and stored until cytokine determination at −70° C.

With the aim of evaluating the functional status of the cells and their capacity of responding to the mitogen in the presence of the test articles at each concentration level, the control cell cultures, containing the test articles in identical concentrations, were incubated for 72 hours following the initial concomitant introduction of ConA and the test substances. 16 hours prior to the incubation completion, $^3$H-thymidine was added, and the label rate of incorporation into DNA was interpreted as the criterion of the cellular test system functional state.

Venous blood from male healthy volunteers was collected into plastic heparinized tubes (endotoxin tested). PMNL fraction was isolated by centrifugation in density gradient of Ficoll and sodium diatrizoate (Histopaque-1077; Sigma).

Cell concentration was adjusted to $2 \times 10^6$ per mL of "complete" culture medium (RPMI 1640, Sigma) containing: HEPES (20 mM); L-glutamine (2mM); Gentamicin (50 $\mu$g/mL); fetal calf serum (10%). All the reagents used were of "cell culture tested" grade, Sigma. Cell viability was estimated by the Trypan blue exclusion method and 100 $\mu$L of cell suspension (200,000 cells) was placed into each well of flat bottom 96-well sterile micro titer plates for tissue cultures. Cells from each subject were placed into no less than 39 wells.

The five following final concentrations of the test articles (GSSG, as well as its drug forms containing 0.003% $H^2O^2$, or 0.1% inosine, or 0.1% cystamine) were evaluated: 5000 $\mu$g/mL; 500 $\mu$g/mL; 50 $\mu$g/mL; 5 $\mu$g/mL; and 0.5 $\mu$g/mL. Each concentration was established in no less than 6 wells by adding 50 $\mu$L of "complete" medium containing the appropriate quantity of the previously dissolved test articles. Another 6 wells were used for control cultures and contained no GSSG: 50 $\mu$L of "complete" medium, or correspondingly, "complete" medium containing 0.003% $H_2O_2$, or 0.1% inosine, or 0.1% cystamine, were added.

Immediately after the test articles had been entered into the cultures, 50 $\mu$L of "complete" medium containing ConA (Sigma, cell culture tested) in a quantity required for a final concentration of 4.0 $\mu$g/mL, was added to all the wells excepting 3 additional ones which served for evaluation of spontaneous $^3$H-thymidine uptake (without ConA).

After a twenty four hour incubation at 37° C. and 5% of $CO_2$, contents of 3 wells (from each sextuplet of identical wells) were taken out, centrifuged, and the supernatants were frozen and kept at −70° C. until the cytokine assay. Cultures in the other 3 wells (of each sextuplet were incubated further under the conditions described above.

Fifty six hours after the incubation had begun, 1.0 $\mu$Ci of $^3$H-thymidine was added into all the remaining cultures, the plates were incubated for another 16 hours, and then the contents of the wells were harvested and transferred onto glass-fiber filters which were consequently treated with 5% trichloroacetic acid and ethanol. The filters were dried and their radioactivity (counts per minute, cpm) was determined using liquid scintillation counter, Betaplate 1205 (LKB).

Mean radioactivity values for triplicates of identical cultures were used to calculate the index of mitogenic stimulation: the ratio of averaged cpm values of ConA stimulated cultures to averaged cpm values of unstimulated ones (3 wells without ConA). This stimulation index for wells, where the test articles were present in various concentrations, served as a criterion of cellular functional status, and ability of the cells to respond to mitogenic stimulation.

Supernatants of 24-hour culture triplicates were subsequently assayed for cytokine content only if their 72-hour matched control culture triplicates developed mitogenic response to ConA with value of the stimulation index in the range from 15 to 50.

Concentrations of interleukin-1b), interleukin-6 (IL-6), tumor necrosis factor $\alpha$ (TNF$\alpha$), and interferon $\alpha$ (IFNα) were determined by ELISA using commercial reagent kits (Medgenix, Belgium) and were expressed in pg/mL of culture supernatants.

The salient findings given in Tables 14. As can be seen from Tables 1 and 2, the adding of GSSG into the culture media resulted in statistically significant and dose-dependent stimulation of the cytokine production by human mononuclear leukocytes. In addition, the presence of hydrogen peroxide leads to increase control (no GSSG) levels of IL-6 and TNF-α. Besides that, being used in combination with hydrogen peroxide GSSG exerts a more pronounced (1.5–2 fold) stimulatory effect on the production of the cytokines on study: for IL-β—at 5.0–5000 μg/ml concentration levels; for IL-6 and TNF-α —in the entire concentration range; and for IFN-α—at 500 and 5000 μg/mL.

The application of GSSG in 0.1% inosine solution and 0.1% cystamine solution results in a significant and dose-dependent increase of cytokine production, particularly with respect to IL-6 and TNFα (Tables 3 and 4).

Thus, the GSSG effect on the human peripheral blood mononuclear leukocytes in vitro manifests in considerable stimulation of the cytokine release into culture media, thereby confirming the stimulatory effect of GSSG on the natural cytokine-producing capacity of the human blood cells. The use of GSSG in combination with hydrogen peroxide, inosine, as well as cystamine results in a more prominent effect of GSSG in respect of induction of endogenous cytokine production.

TABLE 1

GSSG effect on in vitro cytokine production by human mononuclear leukocytes. (M ± m)

| GSSG (μg/mL) | Cytokine production (pg/mL) | | | |
|---|---|---|---|---|
| | IL-1β | IL-6 | TNFa | IFNa |
| 5000 | 259 ± 36.8* | 2518 ± 264* | 1900 ± 206* | 511 ± 64.1* |
| 500 | 275 ± 39.3* | 2113 ± 132* | 1525 ± 163* | 514 ± 56.2* |
| 50 | 202 ± 24.9* | 1910 ± 205* | 813 ± 90.8* | 407 ± 51.4* |
| 5.0 | 88.5 ± 13.5* | 550 ± 61.3* | 314 ± 44.7* | 109 ± 12.1 |
| 0.5 | 56.0 ± 9.1 | 430* ± 55.6 | 99.1 ± 11.6 | 130 ± 14.9 |
| Control (RPMI) | 46.0 ± 6.8 | 129 ± 12.4 | 88.7 ± 9.3 | 98.3 ± 14.0 |

*differences are statistically significant (p < 0.01) as compared to the control.

TABLE 2

Effect of GSSG in combination with 0.003% hydrogen peroxide on in vitro cytokine production by human mononuclear leukocytes. (M ± m)

| GSSG (μg/mL) | Cytokine production (pg/mL) | | | |
|---|---|---|---|---|
| | IL-1β | IL-6 | TNFα | IFNα |
| 5000 | 720 ± 81.3* | 4035 ± 518* | 2640 ± 355* | 849 ± 102* |
| 500 | 650 ± 67.1* | 4007 ± 419* | 2100 ± 294* | 905 ± 141* |
| 50 | 511 ± 55.1* | 3859 ± 425* | 1308 ± 164* | 468 ± 69.3* |
| 5.0 | 212 ± 31.7* | 1680 ± 207* | 502 ± 86.4 | 160 ± 37.0 |
| 0.5 | 63.0 ± 7.8 | 851 ± 111 | 318 ± 47.8 | 98.3 ± 18.7 |
| Control (RPMI + 0.003% H₂O₂) | 51.0 ± 7.4 | 970 ± 140 | 410 ± 57.0 | 125 ± 20.8 |

*differences are statistically significant (p < 0.01) as compared to the control.

TABLE 3

Effect of GSSG in combination with 0.1% inosine on in vitro cytokine production by human mononuclear leukocytes. (M ± m)

| GSSG (μg/ml) | Cytokine production (pg/mL) | | | |
|---|---|---|---|---|
| | IL-1β | IL-6 | TNFα | IFNα |
| 5000 | 665 ± 735* | 5720 ± 498* | 5900 ± 317* | 1010* ± 160.5* |
| 500 | 790 ± 68 55* | 3840 ± 352* | 4520 ± *366 | 1318 ± 152* |
| 50 | 416 ± 44.0* | 4910 ± 205* | 1869 ± 90.8* | 311 ± 51.4* |
| 5.0 | 205 8 ± 18.3* | 2680 ± 196* | 765 ± 67.1* | 117 ± 10.4* |
| 0.5 | 183 ± 20.0* | 1505 ± 138* | 597 ± 48.6* | 66.3 ± 7.8* |
| Control (RPMI + 0.003% H₂O₂) | 60.9 ± 5.59* | 131 ± 11.7* | 83.5 ± 9.6* | 89.5 ± 10.0* |

TABLE 4

TABLE 4 Effect of GSSG in combination with 0.1% cystamine on in vitro cytokine production by human mononuclear leukocytes. (M ± m)

| GSSG (μg/ml) | Cytokine production (pg/mL) | | | |
|---|---|---|---|---|
| | IL-1β | IL-6 | TNFα | IFNα |
| 5000 | 810 ± 75.36* | 4910 ± 503* | 5140 ± 466* | 1060 ± 799* |
| 500 | 540 ± 60.03* | 4000 ± 307* | 3800 ± 307* | 780 ± 180.3* |
| 50 | 490 ± 45.5* | 3800 ± 3183* | 2600 ± 183 | 460 ± 39* |
| 5.0 | 316 ± 30.5* | 2610 ± 207* | 1408 ± 101* | 100 ± 17.7* |
| 0.5 | 155 ± 9.7* | 10 ± 110* | 709 ± 67.3* | 107.6 ± 8.13* |
| Control (RPMI + 0,1% cystamine) | 60.8 ± 6 55* | 65.4 ± 77.0* | 377 ± 28.9* | 114 ± 10.01* |

*differences are statistically significant (p < 0.01) as compared to the control.

EXAMPLE #2

Effect of GSSG and Its Drug Forms on Cytokine and Hemopoietic Factor Production as Well as on Hemopoiesis and Immunity Parameters in Cyclophosphamide-Induced Hemo- and Immunodepression Both oxidized (GSSG) and reduced (GSH) glutathione, as well as GSSG drug forms containing 0.003% hydrogen peroxide, or 0.1% inosine, or 0.1% cystamine, were evaluated in a murine model of hemo- and immunodepression induced by a single administration of cytostatic cyclophosphamide (CP).

The study was designed to evaluate the effect of a 5-day long administration of the test articles on the capability of the CP-treated murine splenocytes to produce IL-2 and GM-CSF in vitro. In addition, the number of blood leukocytes and lymphocytes and the bone marrow cellularity (number of karyocytes) were determined at 8 days after CP administration. Some animals receiving CP were then challenged with sheep red blood cells (SRBC), and the humoral immune response to the antigen was evaluated.

Male CBA mice (18 to 20g body weight) were given a single intraperitoneal injection of CP in a dose of 50 mg/kg. Five groups of animals (with no less than 15 mice in each) were formed. Group description is represented below.

Control groups:
- ☐ #1—intact animals receiving a single injection of normal saline (NS) instead of CP injection, which further were treated with test article vehicle (normal saline);
- ☐ #2—control animals receiving a single CP injection, which further were treated with test article vehicle (normal saline);
- ☐ #3—animals receiving a single CP injection, which further were treated with s reference article (GSH dissolved in normal saline) in a dose of 5 mg/kg;

Test groups:
- ☐ #4—animals receiving a single CP injection, which further were treated with the test article (GSSG dissolved in normal saline) in a dose of 5 mg/kg;
- ☐ #5—animals receiving a single CP injection, which further were treated with a variant of the test article drug form (GSSG dissolved in normal saline containing 0.003% $H_2O_2$) with a GSSG dose of 5 mg/kg;
- ☐ #6—animals receiving a single CP injection, which further were treated with a variant of the test article drug form (GSSG dissolved in normal saline containing 0.1% inosine) with a GSSG dose of 5 mg/kg;
- ☐ #7—animals receiving a single CP injection, which further were treated with a variant of the test article drugform (GSSG dissolved in normal saline containing 0.1% cystamine) with a GSSG dose of 5 mg/kg;

Twenty four hours after the CP injection, 5 animals in each group were immunized with SRBC (107 cells in 0.5 mL of NS, intraperitoneally).

On day 3 after the CP injection (24 hours after the immunization) the intraperitoneal injections of the test or reference articles were started (as it has been described above).

Injections were performed during 5 days: once a day, daily.

Twenty four hours after the completion of 5 day treatment course (on the 8th day after the CP injection), mice were euthanized and splenocyte cultures were aseptically prepared for assessment of spontaneous production of IL-2 and GM-CSF by the spleen lymphocytes in vitro.

Simultaneously, blood and marrow samples were collected for blood leukocyte and lymphocyte, and marrow nucleated cell counted.

Serum samples from immunized animals were tested on level of SRBC agglutinins (the day 8 after the CP injection, and the day 7 after the immunization).

Table #5 shows the parameters of IL-2 and GM-CSF production by splenocytes, bone marrow and blood cellular indices, and the immune response to sheep red blood cells in mice receiving the test articles against the background of cyclophosphamide induced hemo- and immunodepression.

As is seen from the data, the use of both GSSG and GSSG solution in hydrogen peroxide brings IL-2 and GM-CSF splenocytic production almost back to normal whereas GSH shows no such effect. Also, both GSSG and its hydrogen peroxide solution exert a significant restorative effect on the bone marrow and blood parameters as well as immune response to SRBC.

Tables ##6 and 7 give data on effects of pharmacologically active compositions containing GSSG (in combination with 0.1% of inosine, or 0.1% cystamine) on tested parameter variations in mice with CP-induced hemo- and immunodepression. The findings show significant enhancing GSSG effects by inosine and cystamine components with respect of IL-2b and GM-CSF production stimulation and restoration of bone marrow and blood cellularity. As it could be seen, GSH did not exhibit such stimulation. The maximum stimulation was achieved with the combination of GSSG and 0.1% inosine.

Thus, the use of the subject method in CP-induced hemo- and immunocompromised animals results in a prominent stimulation of IL-2 and GM-CSF endogenous production together with restoration of the bone marrow and blood cellular indices as well as immune response development to sheep red blood cells.

TABLE 5

Effect of the test articles on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSGO + $H_2O_2$ |
| IL-2 production by splenocytes, (U/mL) | 10 | 39.7 ± 5.4 | 11.1 ± 3.0* | 17.2 ± 3.5* | 28.1 ± 3.9#@ | 34.7 ± 5.1#@ |
| GM-CSF production by splenocytes, (colonies/$10^5$ | 10 | 180.0 ± 14.2 | 34.3 ± 9.1* | 58.2 ± 7.2* | 129.1 ± 13.4#@ | 170.1 ± 16.9#@ |

TABLE 5-continued

Effect of the test articles on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSGO + $H_2O_2$ |
| cells) | | | | | | |
| Blood leukocyte count, $10^9$/L | 10 | 11.9 ± 1.81 | 4.7 ± 1.25* | 5.2 ± 1.36* | 8.5 ± 0.81#@ | 9.4 ± 1.40#@ |
| Blood lymphocyte count, $10^9$/L | 10 | 7.4 ± 0.85 | 3.1 ± 0.56* | 4.3 ± 1.13* | 6.2 ± 1.28# | 6.8 ± 1.04# |
| Bone marrow nucleated cell number, $10^6$/L | 10 | 53.7 ± 8.7 | 23.8 ± 5.0* | 32.2 ± 4.4* | 45.4 ± 3.9#@ | 52.3 ± 4.7#@ |
| SRBC agglutinin titer ($\log_2$) | 5 | 5.33 ± 0.74 | 1.47 ± 0.35* | 1.94 ± 0.34* | 3.68 ± 0.59*# | 4.12 ± 0.37*# |

Differences are statistically significant ($p < 0.05$) as compared:
(*) — to the group of intact animals; (#) — to the control group (CP + normal saline); (@) — to the group of animals treated with GSH.

TABLE 6

Effect of GSSG in combination with 0.1% inosine on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSG + 0.1% inosine |
| IL-2 production by splenocytes, (U/mL) | 10 | 34.4 ± 4.2 | 9.2 ± 1.9* | 15.3 ± 2.7* | 29.8 ± 3.158#@ | 39.7 ± 4.8#@ |
| GM-CSF production by splenocytes, (colonies/$10^5$ cells) | 10 | 168.0 ± 14.9 | 25.5 ± 4.2* | 63.4 ± 7.8* | 143 ± 15.06#@ | 196.3 ± 16.6#@ |
| Blood leukocyte count, $10^9$/L | 10 | 123 ± 14 | 5.03 ± 0.85* | 6.3 ± 0.05* | 9.5 ± 1.01#@ | 10.1 ± 1.36#@ |
| Blood lymphocyte count, $10^9$/L | 10 | 8.2 ± 0.09 | 2.8 ± 0.67* | 4.6 ± 0.78* | 6.7 ± 0.81# | 7.18 ± 0.74# |
| Bone marrow nucleated cell number, $10^6$/L | 10 | 61.3 ± 8.05 | 19.7 ± 2.9* | 36.4 ± 4.5* | 48.99 ± 5.14#@ | 69.4 ± 17.7#@ |
| SRBC agglutinin titer ($\log_2$) | 5 | 6.03 ± 0.71 | 1.05 ± 0.28* | 1.62 ± 0.27* | 4.08 ± 0.58*# | 5.13 ± 053*# |

Differences are statistically significant ($p < 0.05$) as compared:
(*) — to the group of intact animals; (#) — to the control group (CP + normal saline); (@) — to the group of animals treated with GSH.

TABLE 7

Effect of GSSG in combination with 0.1% cystamine on IL-2 and GM-CSF production by splenocytes, bone marrow and blood cellular indices, and immune response to SRBC in cyclophosphamide treated mice. (M ± m)

| Parameter | n | Intact animals Normal saline | Cyclophosphamide-treated animals | | | |
|---|---|---|---|---|---|---|
| | | | Normal saline | GSH | GSSG | GSSG + 0.1% cystamine |
| IL-2 production by splenocytes, (U/mL) | 10 | 43.5 ± 4.01 | 14.0 ± 2.7* | 20.3 ± 2.6* | 30.9 ± 3.03#@ | 38.8 ± 4.53#@ |
| GM-CSF production by splenocytes, (colonies/$10^5$ cells) | 10 | 190.5 ± 18.4 | 42.0 ± 5.7* | 66.7 ± 7.8* | 137.0 ± 13.09#@ | 183.7 ± 17.8#@ |
| Blood leukocyte count, $10^9$/L | 10 | 12.3 ± 1.28 | 4.95 ± 0.88* | 6.2 ± 1.06* | 7.8 ± 0.84#@ | 10.5 ± 1.56#@ |
| Blood lymphocyte count, $10^9$/L | 10 | 8.2 ± 0.72 | 3.6 ± 0.63* | 5.31 ± 0.77* | 7.2 ± 0.96# | 7.8 ± 0.84# |
| Bone marrow nucleated cell number, $10^6$/L | 10 | 61.3 ± 5.9 | 28.5 ± 4.2* | 36.4 ± 4.5* | 48.9 ± 5.14#@ | 56.7 ± 4.91#@ |
| SRBC agglutinin titer ($\log_2$) | 5 | 6.03 ± 0.60 | 1.78 ± 0.36* | 2.09 ± 0.37* | 4.08 ± 0.57*# | 4.29 ± 0.41*# |

Differences are statistically significant (p < 0.05) as compared:
(*) — to the group of intact animals; (#) — to the control group (CP + normal saline); (@) — to the group of animals treated with GSH.

EXAMPLE #3

Effect of GSSG and Its Drug Forms on Cytokine and Hemopoietic Factor Production as Well as on Hemopoiesis and Immunity Parameters in Radiation-Induced Hemo- and Immunodepression Both oxidized (GSSG) and reduced (GSH) glutathione, as well as GSSG drug forms containing 0.003% hydrogen peroxide, or 0.1% inosine, or 0.1% cystamine, were evaluated in a murine model of hemo- and immunodepression induced by a single irradiation in a total dose of 1 Gy.

The study was designed to evaluate efficacy of 7-day daily administration of the test articles (with the dosing started 2 hours post-exposure) on the capability of the splenocytes from mice exposed to radiation to produce IL-2 and GM-CSF in vitro. In addition, the number of blood leukocytes and lymphocytes and the spleen and bone marrow cellularity (number of karyocytes), as well as splenic and medullary colony-stimulating capacity, were determined at 8 days post-exposure.

Male CBA mice (18 to 20 g body weight) were irradiated with single dose of 180 kV X-rays filtered with 0.5mm Cu (at 15 mA, distance—70 cm, duration 2 min. and 28 sec.).

The total absorbed dose comprised approximately 1 Gy.

Five groups of animals (with no less than 12 mice in each) were formed. Group description is represented below.

Control groups:
- #1—intact animals receiving a sham irradiation procedure to reproduce a stress impact, which further were treated with test article vehicle (normal saline);
- #2—control animals irradiated in a dose of 1 Gy, which further were treated with test article vehicle (normal saline);
- #3—animals irradiated in a dose of Gy, which further were treated with s reference article (GSH dissolved in normal saline) in a dose of 5 mg/kg;

Test groups:
- #4—animals irradiated in a dose of Gy, which further were treated with the test article (GSSG dissolved in normal saline) in a dose of 5 mg/kg;
- #5—animals irradiated in a dose of Gy, which further were treated with a variant of the test article drugform (GSSG dissolved in normal saline containing 0.003% $H_2O_2$) with a GSSG dose of 5 mg/kg;
- #6—animals irradiated in a dose of Gy, which further were treated with GSSG in normal saline containing 0.1% inosine) with a GSSG dose of 5 mg/kg;
- #7—animals irradiated in a dose of 1 Gy, which further were treated with GSSG in normal saline containing 0.1% cystamine) with a GSSG dose of 5 mg/kg;

Two hours after the irradiation the intraperitoneal injections of the test or reference articles were started (as it has been described above). Injections were performed during 7 days: once a day, daily.

Twenty four hours after the completion of 7 day treatment course (on the 8th day after the irradiation), mice were euthanized and splenocyte cultures were aseptically prepared for assessment of spontaneous production of IL-2 and GM-CSF by the spleen lymphocytes in vitro.

Simultaneously, blood, spleen and marrow samples were collected for blood leukocyte and lymphocyte, and spleen and marrow nucleated cell counting.

Additionally, hemopoietic colony formation ability of spleen and bone marrow cells was assessed by the method of direct count of colony forming units (CFU) in the spleens of irradiated CBA mice receiving intravenously spleen or bone marrow cells obtained from animals of control or test groups.

Splenocytic IL-2 and GM-CSF levels, blood, bone marrow, and spleen cellular indices as well as colony-stimulating capacity numbers (colony-forming units, CFU) in the bone marrow and spleen of the irradiated animals at 8 days post-exposure, are summarized in Tables 8, 9, 10.

TABLE 8

Effect of the test articles on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals | | | |
|---|---|---|---|---|---|---|
| | | | Normal saline | GSH | GSSG | GSSGO + $H_2O_2$ |
| IL-2 production by splenocytes, (U/mL) | 12 | 41.2 ± 4.4 | 5.0 ± 0.5* | 8.6 ± 1.3* | 25.1 ± 4.9*#@ | 37.1 ± 3.4#@ |
| GM-CSF production by splenocytes, (colonies/$10^5$ cells) | 12 | 120.2 ± 12.4 | 20.7 ± 8.6* | 31.8 ± 3.9* | 93.1 ± 11.5#@ | 106.4 ± 5.2#@ |
| Blood leukocyte count, $10^9$/L | 12 | 12.7 ± 1.3 | 3.4 ± 0.9* | 4.8 ± 0.8* | 8.7 ± 1.3*#@ | 10.7 ± 2.0#@ |
| Blood lymphocyte count, $10^9$/L | 12 | 7.9 ± 0.7 | 2.2 ± 1.3* | 3.4 ± 0.6* | 5.9 ± 0.8#@ | 6.9 ± 0.8#@ |
| Spleen nucleated cell number, $10^7$/L | 12 | 9.8 ± 1.5 | 4.8 ± 1.3* | 4.3 ± 1.5* | 7.7 ± 1.2#@ | 8.2 ± 2.0#@ |
| Bone marrow nucleated cell number, $10^6$/L | 12 | 45.1 ± 3.2 | 14.0 ± 1.0* | 17.2 ± 3.5* | 33.3 ± 5.2*#@ | 37.0 ± 4.0#@ |
| Bone marrow CFU | 12 | 59.4 ± 3.2 | 11.6 ± 2.2* | 22.1 ± 3.6* | 44.3 ± 3.9*#@ | 49.3 ± 3.9#@ |
| Spleen CFU | 12 | 93.2 ± 4.1 | 40.0 ± 5.4* | 56.3 ± 6.8* | 88.3 ± 6.8#@ | 87.6 ± 4.7#@ |

Differences are statistically significant ($p < 0.05$) as compared:
(*) — to the group of intact animals; (#) — to the control group (CP + normal saline); (@) — to the group of animals treated with GSH.

TABLE 9

Effect of GSSG in combination with 0.1% cystamine on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals | | | |
|---|---|---|---|---|---|---|
| | | | Normal saline | GSH | GSSG | GSSG + 0.1% cystamine |
| IL-2 production by splenocytes, (U/mL) | 12 | 45.4 ± 4.2 | 5.6 ± 0.71* | 9.3 ± 1.44* | 29.3 ± 3.18*#@ | 40.1 ± 4.10#@ |
| GM-CSF production by splenocytes, (colonies/$10^5$ cells) | 12 | 132 ± 11.8 | 28.6 ± 4.5* | 34.3 ± 3.99* | 103 ± 11.6#@ | 113 ± 9.07#@ |
| Blood | 12 | 13.3 ± 1.08 | 3.1 ± 0.9* | 5.7 ± 0.9* | 9.3 ± 4.5*#@ | 11.2 ± 1.83#@ |

TABLE 9-continued

Effect of GSSG in combination with 0.1% cystamine on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals Normal saline | GSH | GSSG | GSSG + 0.1% cystamine |
|---|---|---|---|---|---|---|
| leukocyte count, $10^9$/L | | | | | | |
| Blood lymphocyte count, $10^9$/L | 12 | 8.6 ± 0.74 | 3.38 ± 0.61* | 4.6 ± 0.70* | 6.79 ± 0.82[#@] | 7.12 ± 0.899[#@] |
| Spleen nucleated cell number, $10^7$/L | 12 | 10.5 ± 0.97 | 5.8 ± 0.9* | 6.93 ± 0.85* | 8.9 ± 1.07[#@] | 10.7 ± 1.13[#@] |
| Bone marrow nucleated cell number, $10^6$/L | 12 | 48.3 ± 3.8 | 15.1 ± 1.69* | 24.7 ± 3.0* | 39.5 ± 4.17*[#@] | 51.0 ± 4.81[#@] |
| Bone marrow CFU | 12 | 61.3 ± 5.2 | 16.0 ± 2.5* | 25.6 ± 3.99* | 50.3 ± 5.14*[#@] | 55.7 ± 5.31[#@] |
| Spleen CFU | 12 | 104 ± 9.2 | 43.5 ± 5.8* | 66.3 ± 7.07* | 94.0 ± 8.81[#@] | 107 ± 11.7[#@] |

Differences are statistically significant (p < 0.05) as compared:
(*) — to the group of intact animals; (#) — to the control group (CP + normal saline); (@) — to the group of animals treated with GSH.

TABLE 10

Effect of GSSG in combination with 0.1% inosine on IL-2 and GM-CSF production by splenocytes, bone marrow, spleen and blood cellular indices, and bone marrow and spleen hematopoietic colony formation capability in irradiated mice. (M ± m)

| Parameter | n | Sham-irradiated animals Normal saline | Irradiated animals Normal saline | GSH | GSSG | GSSG + 0.1% inosine |
|---|---|---|---|---|---|---|
| IL-2 production by splenocytes, (U/mL) | 12 | 45.1 ± 4.3 | 4.6 ± 0.53* | 9.9 ± 1.08* | 26.9 ± 3.4*[#@] | 44.3 ± 4.71[#@] |
| GM-CSF production by splenocytes, (colonies/$10^5$ cells) | 12 | 132 ± 11.9 | 21.8 ± 3.7* | 35.9 ± 4.15* | 116 ± 11.7[#@] | 163 ± 22.1[#@] |
| Blood leukocyte count, $10^9$/L | 12 | 12.0 ± 1.4 | 3.04 ± 0.81* | 4.95 ± 0.62* | 7.93 ± 0.96*[#@] | 10.9 ± 2.04[#@] |
| Blood lymphocyte count, $10^9$/L | 12 | 8.15 ± 0.76 | 1.94 ± 0.51* | 4.0 ± 0.58* | 6.7 ± 0.83[#@] | 7.8 ± 0.86[#@] |
| Spleen nucleated cell number, $10^7$/L | 12 | 9.91 ± 1.3 | 3.5 ± 0.66* | 5.5 ± 0.70* | 9.0 ± 1.13[#@] | 10.2 ± 1.5[#@] |
| Bone marrow nucleated cell number, $10^6$/L | 12 | 47.3 ± 3.18 | 13.0 ± 1.8* | 22.5 ± 3.08* | 39.9 ± 4.5*[#@] | 51.7 ± 4.98[#@] |
| Bone marrow CFU | 12 | 56.2 ± 4.4 | 9.7 ± 1.3* | 25.3 ± 3.7* | 48.9 ± 5.13*[#@] | 69.0 ± 7.03[#@] |
| Spleen CFU | 12 | 154 ± 9.45 | 35.0 ± 5.14* | 59.8 ± 6.18* | 99.3 ± 10.11[#@] | 167.0 ± 17.3[#@] |

Differences are statistically significant (p < 0.05) as compared:
(*) — to the group of intact animals; (#) — to the control group (CP + normal saline); (@) — to the group of animals treated with GSH.

As is evident from the data of the tables, administration of GSSG, or its drug forms containing 0.003% hydrogen peroxide, or 0.1% inosine, or 0.1% cystamine, results in statistically significant recovery of IL-2 and GM-CSF production by splenocytes, whereas GSH produces no significant effect.

Furthermore, both GSSG alone and its pharmacologically active compositions exerted a significant normalizing effect on the blood, spleen, and bone marrow cellularity. In several instances the effect of GSSG dissolved in hydrogen peroxide has been found to be more prominent. For example, while GSSG per se exhibited no statistically significant effect (as compared to controls) on IL-2 splenocytic production, blood leukocytes, bone marrow cellularity, and bone marrow colonies, GSSG in hydrogen peroxide did produce a statistically meaningful effect. If compared with hydrogen peroxide, both inosine and cystamine were found to exert more prominent effect of enhancing the GSSG action, with the maximal effect being achieved in case of active composition of GSSG with inosine.

Thus, the use of the subject method in animals developed radiation-induced hemo- and immunodepression results in pronounced stimulation of the endogenous IL-2 and GM-CSF production, and also leads to an accelerated recovery of the cellular compositions of the blood, lymphoid and hemopoietic organs as well as colony-forming activity of the bone marrow and spleen.

EXAMPLE #4

Effect of GSSG and Its Drug Forms on the Process of Proliferation and Apoptosis of Normal and Tumor Cells The ability of oxidized glutathione (GSSG), as well as its drug forms containing 0.003% hydrogen peroxide, or 0.1% inosine or 0.1% cystamine, to influence processes of a cellular proliferation and/or death was evaluated using normal or tumor cells. To this end, GSSG, or its drug forms had been incubated for 24 hours with cells of myeloid line HL-60 and normal human lymphocytes isolated form peripheral blood of healthy volunteers. Subsequent evaluation of the cell cycle parameters was carried out by the flow cytofluorometry technique.

Venous blood of a healthy volunteer was collected into heparinized test-tubes which had been tested for endotoxin. A mononuclear fraction of blood leukocytes were obtained by centrifugation in gradient of fikoll-metrizoat (Histopaque, Sigma). Cell concentration was adjusted to $2\times10^6$ cells per 1 ml of "complete" cell culture medium (RPMI 1640), containing 20 mM HEPES, 2 mM glutamine, 50 $\mu$g/mL gentamicin and 10% fetal calf serum. Cell viability was estimated by the Trypan blue exclusion method, then the cell suspension was placed into wells of 96-well microtiter plates—200,000 cells per well. Cells of HL-60 line were grown in RPMI-1640 medium with the addition of 10% fetal calf serum. Cultivation was carried out in closed flasks, the medium volume was 12 mL, it was changed every four days by centrifugation. The nature of the cells growth was suspensive. Evaluation of the test solution of GSSG (5000 $\mu$g/mL), as well as GSSG solutions containing 0.003% hydrogen peroxide, or 0.1% cystamine, was carried out using 6 cellular samples of normal lymphocytes and HL-60 cells for each test solution. 50 $\mu$L of each test solution were added to one or the other cell culture and thereafter cells were cultivated for 24–96 hours. Then, they were tested by the flow cytofluorometry to estimate DNA content in the cell nuclei. In case of apoptosis-like cellular death, the portion of cell nuclei with normal content of DNA became reduced, while the portion of cell nuclei containing abnormally small DNA quantity became larger.

The analysis procedure was the following: after incubation completion, cells were centrifuged and transferred to a standard phosphate isotonic buffer pH 7.4, containing RNA-ase A (20 $\mu$g/mL), ethidium bromide (fluorometric indicator for double stranded nucleic acid, 10 $\mu$g/mL) and $MgCl_2$ (5 mM). After the cells were disintegrated by nonionic detergent Triton X-100 (final concentration 0.1%). The suspension of cell nuclei thus obtained was analyzed by flow cytofluorometry with an argon laser as a source of light (wave length 488 nm). The red fluorescence due to DNA bound ethidium bromide was taken to be the measure of DNA content in the cell nuclei. In addition, corresponding samples were studied microscopically for revealing concomitant changes in cell morphology.

The study results are presented in Tables 11, 12 and FIG. 1). The table 11 shows the presence of GSSG or its drug forms promoted proliferation of normal lymphocytes of healthy volunteers, which resulted in increase in their number, while flow cytofluorometry analysis did not reveal any changes characteristic for apoptosis-like cell death (FIG. 1c–d).

Figure 1A:
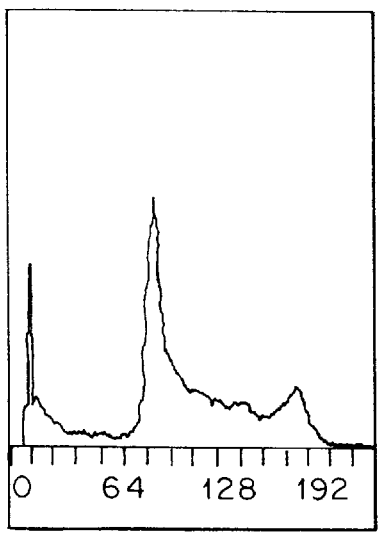
FIGS. 1a, 1b, 1c and 1d are charts showing fluorometric analysis of cells HL-60, cytofluorometric analysis of cells HL-60 in the presence of the preparation of this invention, cytofluorometric analysis of human lymphocytes, and cytofluorometric analysis of lymphocytes in the presence of the preparation of this invention, respectively, as will be described in the discussion of Example 4, relating to research of apoptosis-induced preparation activity in cultivated mammalian cells.
Figure 1B:
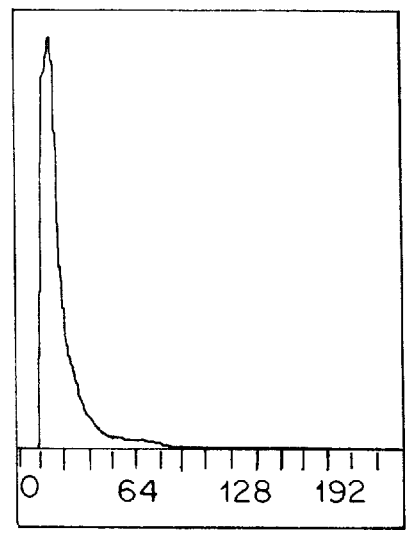
Figure 1C:
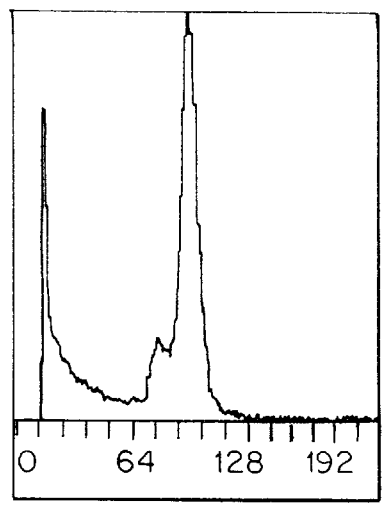
Figure 1D:
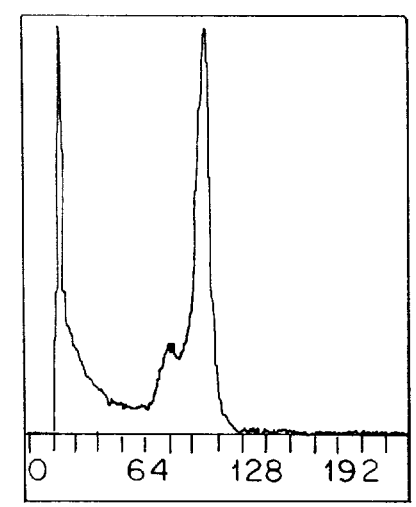

Observation carried out on cell cultures of the tumor cells of myeloid line HL-60 revealed ability of GSSG (as well as its drug forms) to slowdown the proliferation of transformed cells. Table 12 shows that GSSG compositions with hydrogen peroxide, inosine and cystamine inhibit cell HL-60 proliferation better than GSSG alone. The flow cytofluorometry analysis demonstrates the slowdown of cell growth of the HL-60 line cells was associated with characteristic morphological indications of apoptosis-like death: sphere-like cells became multi-fragmented with plural interceptions, the number of cell nuclei with normal content of DNA fell down, while there was an increase in portion of nuclei with abnormally low DNA content (FIG. 1a–1b).

TABLE 11

Effect of the test articles on number of normal lymphocytes per well ($\times 10^4$ cells) throughout the 96-hr incubation. (M ± m)

| Test articles (solutions) | 24 hours | 48 hours | 72 hours | 96 hours |
| --- | --- | --- | --- | --- |
| GSSG in normal saline | 27 ± 2 | 98 ± 6* | 176 ± 12 | 386 ± 18* |
| GSSG + 0,003% $H_2O_2$ | 25 ± 4 | 108 ± 8* | 231 ± 14* | 419 ± 21* |
| GSSG + 0.1% inosine | 28 ± 3 | 107 ± 5* | 212 ± 16* | 306 ± 12* |
| GSSG + 0.1% cystamine | 26 ± 3 | 93 ± 5* | 186 ± 10* | 263 ± 14* |
| 0,003% $H_2O_2$ | 28 ± 2 | 73 ± 5 | 123 ± 8 | 206 ± 8 |
| 0.1% inosine | 26 ± 4 | 78 ± 7 | 141 ± 12 | 216 ± 16 |
| 0.1% cystamine | 30 ± 2 | 72 ± 4 | 122 ± 9 | 196 ± 11 |
| 10% fetal calf serum | 29 ± 4 | 74 ± 7 | 133 ± 18 | 263 ± 13 |

*Differences are statistically significant (p < 0.05) as compared to 10% fetal calf serum.

TABLE 12

Effect of the test articles on number of HL-60 cells per well ($\times 10^4$ cells) throughout the 96-hr incubation. (M ± m)

| Test articles (solutions) | 24 hours | 48 hours | 72 hours | 96 hours |
| --- | --- | --- | --- | --- |
| GSSG in normal saline | 102 ± 4 | 156 ± 6* | 386 ± 21* | 390 ± 11* |
| GSSG + 0,003% $H_2O_2$ | 96 ± 6* | 132 ± 4* | 286 ± 18* | 306 ± 18* |
| GSSG + 0.1% inosine | 49 ± 3* | 76 ± 6* | 138 ± 11* | 165 ± 9* |
| GSSG + 0.1% cystamine | 68 ± 8* | 102 ± 11* | 242 ± 19* | 256 ± 14* |

TABLE 12-continued

Effect of the test articles on number of HL-60 cells per well (×10⁴ cells) throughout the 96-hr incubation. (M ± m)

| Test articles (solutions) | 24 hours | 48 hours | 72 hours | 96 hours |
|---|---|---|---|---|
| 0,003% $H_2O_2$ | 122 ± 6 | 186 ± 12 | 488 ± 24 | 712 ± 22 |
| 0.1% inosine | 96 ± 8* | 152 ± 8* | 312 ± 21* | 527 ± 18* |
| 0.1% cystamine | 112 ± 10 | 182 ± 9 | 465 ± 11 | 618 ± 19 |
| 10% fetal calf serum | 119 ± 7 | 181 ± 13 | 471 ± 7 | 752 ± 16 |

*Differences are statistically significant ($p < 0.05$) as compared to 10% fetal calf serum.

Thus, the results obtained enable to declare the dual functional properties of GSSG and its drug forms which selectively induce proliferation slowdown and apoptosis-like death of tumor cells while accelerate proliferation of normal human cells (lymphocytes) without any signs of their apoptosis. The application of GSSG in combination with inosine produces the most prominent effect of GSSG in respect of normal cells.

EXAMPLE #5

Effect of GSSG and Its Drug Forms on Progression of Experimental Tumors in Mice

An antitumor activity of GSSG, as well as its drug forms containing 0.003% hydrogen peroxide or 0.1% inosine, or 0.1% cystamine, was evaluated in the two mouse models of the tumor process induced by the intraperitoneal inoculation of leukemia P388 and leukemia L1210 cells. An influence of 7 day course of test article daily administration was studied in respect of variations of serum cytokine levels (IL-1, IL-2, IL-6, IFNα, TNF). In parallel, the tumor progression was estimated using the two integral indices: pace of mouse weight gain due to accumulation of ascitic fluid, and by animal mean survival time after inoculation.

The study was carried out on DBA/2 mice weighing 18–21 g. First, tumor cell passage was performed using 6 animals for each cell line. For this, cells kept at the temperature of the liquid nitrogen were de-frozen and adjusted to the concentration of $5 \times 10^6$ cells/mL by sterile Hanks' solution. Then, 6 mice were intraperitoneally inoculated with 0.2 mL of each line cellular suspension.

Ascitic fluid was collected 6 days after the inoculation with L1210 cells and 8 days after the inoculation with P388 ones. Thus obtained, the samples of passaged tumor cells were used for the main experiments. The fluid liquid was dissolved by sterile Hanks' solution so that cell concentration be $5 \times 10^6$ cells/mL for P388 cells and $5 \times 10^5$ cells/mL for L1210 cells.

Nine groups of animals with no less than 15 mice each were formed for experiments with either tumor cell line. Mice were inoculated with 0.2 mL of resultant cell suspensions per mouse ($10^6$ P388 cells/mouse, and $10^5$ L1210 cells/mouse). 24 hours after the tumor cells inoculation, animals were given the first injections of the test articles or vehicles. The test article injections were made daily till the 14th day of the experiment or until the animal's death. The volume of solutions injected comprised 0.01 mL/g body weight. Description of nine groups of animals formed for experiments with either tumor cell line is given below.

Control groups:
- ☐ #1—intact animals receiving imitation of tumor cell inoculation (injection of normal saline) which further were treated with normal saline throughout the entire experiment;
- ☐ #2—control animals, inoculated with tumor cells, which further were treated with test article vehicle (normal saline);

Control groups:
- ☐ #3—experimental animals, inoculated with tumor cells, which further were treated with test article (GSSG dissolved in normal saline) in a dose of 5 mg/kg;
- ☐ #4—experimental animals, inoculated with tumor cells, which further were treated with a variant of test article drug form (GSSG dissolved in normal saline containing 0.003% of hydrogen peroxide), with a GSSG dose of 5 mg/kg;
- ☐ #5—experimental animals, inoculated with tumor cells, which further were treated with a variant of test article drug form (GSSG dissolved in normal saline containing 0.1% of inosine), with a GSSG dose of 5 mg/kg;
- 58 #6—experimental animals, inoculated with tumor cells, which further were treated with a variant of test article drug form (GSSG dissolved in normal saline containing 0.1% cystamine), with a GSSG dose of 5 mg/kg;
- ☐ #7—experimental animals, inoculated with tumor cells, which further were treated with a variant of drug form component (normal saline containing 0.03% of hydrogen peroxide), without GSSG;
- ☐ #8—experimental animals, inoculated with tumor cells, which further were treated with a variant of drug form component (normal saline containing 0.1% of inosine), without GSSG;
- ☐ #9—experimental animals, inoculated with tumor cells, which further were treated with a variant of drug form component (normal saline containing 0.1% of cystamine), without GSSG;

Tables 13 and 14 contain results on test article efficacy evaluation as to variations of cytokine endogenous production, as well as data on integral parameters of the tumor process progression. The results obtained show that both GSSG and its drug forms have a substantial cytokine inducing effect, reliably retard (if compared to the control groups) the accumulation of ascitic fluid and increase the mean survival time. GSSG alone and GSSG together with 0.003% of hydrogen peroxide increase more remarkably the IL-1 and IFNα serum levels, whereas GSSG in combination with 0.1% inosine and 0.1% cystamine cause a larger increase in IL-2, IL-6, TNFα serum levels.

The most prominent antitumor effect in respect to slow-down of ascitic fluid accumulation and prolongation of the mean survival time for either tumor models (P388 and L1210 leukemia) were obtained with GSSG in combination with 0.1% cystamine.

TABLE 13

Effect of the test articles on the cytokine serum levels, the accumulation of ascitic fluid and the mean survival time of mice inoculated with leukemia L1210 cells (M ± m)

| Group of animals 1 | The number of injections 2 | Concentration of factors in serum, (pg/mL): | | | | | Accumulation of ascitic fluid (weight gain, %) 8 | Mean survival time 9 |
|---|---|---|---|---|---|---|---|---|
| | | IL-1 3 | IL-2 4 | IL-6 5 | IFNα 6 | TNFα 7 | | |
| Control animals | 0 | 22.0 ± 3.15 | 14.50 ± 2.56 | 93.20 ± 10.58 | 82.2 ± 9.05 | 79.70 ± 8.15 | 0.7 ± 0.1 | 9.02 ± 0.19 |
| | 3 | 28.5 ± 4.01 | 23.18 ± 3.11 | 108.0 ± 14.12 | 100.55 ± 11.34 | 80.3 ± 8.81 | 7.14 ± 0.9 | |
| | 7 | 13.4 ± 2.68 | 17.8 ± 2.51 | 136.70* ± 15.2 | 140.3 ± 16.25 | 196.90 ± 21.30 | 25.4 ± 2.62 | |
| Intact animals | 0 | 20.09 ± 1.95 | 13.14 ± 1.12 | 84.0 ± 9.65 | 108.0 ± 11.33 | 77.90 ± 6.85 | 0.2 ± 0.1 | 35 ± 0 |
| | 3 | 25.10 ± 2.31 | 21.75 ± 1.44 | 85.60 ± 9.01 | 101.0 ± 8.72 | 89.0 ± 7.13 | 1.12 ± 0.3 | |
| | 7 | 21.30 ± 2.98 | 21.15 ± 1.86 | 84.9 ± 7.16 | 90.0 ± 10.11 | 116. ± 10.83 | 4.6 ± 1.23 | |
| GSSG | 0 | 27.5 ± 3.60 | 14.7 ± 3.13 | 124.40 ± 13.7 | 144.80 ± 15.34 | 98.10 ± 11.54 | 0.77 ± 0.16 | 10.74 ± 0.51* |
| | 3 | 57.6 ± 7.14 | 57.7 ± 6.80 | 301.0 ± 32.2 | 508.0* ± 54.3 | 397.0* ± 44.50 | 4.02* ± 0.53 | |
| | 7 | 167.5 ± 18.30 | 144.5 ± 17.03 | 678. ± 74.5 | 1207.0* ± 116.3 | 610.0* ± 71.9 | 15.67* ± 1.70 | |
| GSSG + 0.003% H₂O₂ | 0 | 19.8 ± 2.05 | 14.84 ± 2.13 | 108.0 ± 9.17 | 119.40 ± 9.56 | 78.0 ± 6.15 | 0.44 ± 0.16 | 11.13 ± 0.49* |
| | 3 | 126.0 ± 13.9 | 99.0 ± 11.3 | 298. ± 24.5 | 238.0 ± 18.9 | 406.* ± 35.3 | 3.17* ± 0.41 | |
| | 7 | 123.5 ± 12.7 | 189.0 ± 21.4 | 445. ± 4.14 | 1413*. ± 129. | 818* ± 73.5 | 14.04* ± 1.1 | |
| GSSG + 0.1% inosine | 0 | 25.5 ± 2.86 | 17.40 ± 1.92 | 104. ± 8.15 | 122.4 ± 10.43 | 121.9 ± 10.33 | 0.63 ± 0.16 | 12.01 ± 0.49* |
| | 3 | 83.10 ± 9.15 | 40.8 ± 5.0 | 512.* ± 48.7 | 628.* ± 56.4 | 565.* ± 50.03 | 1.75* ± 0.25 | |
| | 7 | 238.0 ± 29.56 | 91.1 ± 11.08 | 106. ± 9.14 | 1650.* ± 148 | 1904.* ± 186.0 | 5.69* ± 0.74 | |
| GSSC + 0.1% cystamine | 0 | 23.14 ± 2.86 | 17.0 ± 1.55 | 102. ± 8.04 | 129.0 ± 9.80 | 101.5 ± 8.16 | 0.76 ± 0.19 | 11.96 ± 0.59* |
| | 3 | 118.0 ± 13.42 | 59.16 ± 7.55 | 145. ± 11.8 | 761* ± 59.4 | 357.0* ± 28.30 | 2.47* ± 0.28 | |
| | 7 | 189.20 ± 21.0 | 249. ± 22.7 | 400.0* ± 32.5 | 1700.* ± 163. | 709.0* ± 59.0 | 6.85* ± 0.91 | |
| 0.003% H₂O₂ | 0 | 17.07 ± 1.65 | 16.18 ± 1.68 | 120.9 ± 10.7 | 133.7 ± 10.45 | 110. ± 9.13 | 0.79 ± 0.17 | 9.7 ± 0.21 |
| | 3 | 38.15 ± 4.11 | 23.5 ± 3.3 | 140. ± 13.3 | 189. ± 15.45 | 158.0 ± 11.97 | 6.12 ± 0.73 | |
| | 7 | 23.6 ± 3.05 | 45.5 ± 5.8 | 103. ± 9.18 | 209. ± 18.30 | 220.0 ± 24.5 | 21.61 ± 2.55 | |
| 0.1% inosine | 0 | 41.0 ± 4.23 | 17.80 ± 1.49 | 108. ± 9.03 | 117.3 ± 10.81 | 104.3 ± 9.17 | 0.61 ± 0.14 | 9.61 ± 0.18 |
| | 3 | 55.6 ± 6.17 | 22.3 ± 2.14 | 91.0 ± 8.8 | 160.0 ± 12.47 | 130.0 ± 10.85 | 7.02 ± 0.64 | |
| | 7 | 36.40 ± 4.81 | 14.6 ± 1.53 | 119. ± 10.5 | 205. ± 21.3 | 157.0 ± 15.80 | 26.30 ± 2.57 | |
| 0.1% cystamine | 0 | 36.0 ± 3.12 | 16.9 ± 1.5 | 63.0 ± 5.0 | 115.0 ± 10.52 | 88.6 ± 5.19 | 0.47 ± 0.18 | 9.53 ± 0.18 |
| | 3 | 47.50 ± 5.17 | 17.30 ± 1.46 | 70.0 ± 12.6 | 200. ± 18.0 | 185.0 ± 16.70 | 5.93 ± 0.47 | |
| | 7 | 28.0 ± 3.0 | 22.8 ± 1.90 | 155.0 ± 13.4 | 137.0 ± 14.5 | 213.0 ± 18.54 | 21.17 ± 2.05 | |

Differences are statistically significant ($p < 0.05$) as compared as compared to the control group

TABLE 14

Effect of the test articles on the cytokine serum levels, the accumulation of ascitic fluid and the mean survival time of mice inoculated with leukemia P388 cells (M ± m)

| Group of animals 1 | The number of injections 2 | Concentration of factors in serum, (pg/mL) | | | | | Accumulation of ascitic fluid (weight gain, %) 8 | Mean survival time 9 |
|---|---|---|---|---|---|---|---|---|
| | | IL-1 3 | IL-2 4 | IL-6 5 | IFNα 6 | TNFα 7 | | |
| Control animals | 0 | 19.6 ± 3.85 | 10.5 ± 1.59 | 86.18 ± 7.13 | 90.5 ± 7.76 | 85.0 ± 6.15 | 0.5 ± 0.07 | 9.6 ± 0.22 |
| | 3 | 34.7 ± 5.42 | 26.7 ± 3.18 | 133.0 ± 15.2 | 113.0 ± 12.0 | 96.17 ± 8.2 | 6.9* ± 0.52 | |
| | 7 | 10.8 ± 2.34 | 20.3 ± 3.08 | 156.10* ± 20.0 | 158 ± 10.8 | 218* ± 22.03 | 28.2* ± 2.9 | |
| Intact animals | 0 | 25.12 ± 1.76 | 17.70 ± 1.84 | 104.50 ± 9.94 | 90.50 ± 7.19 | 88.64 ± 7.14 | 0.3 ± 0.2 | 35* ± 0 |
| | 3 | 33.0 ± 3.57 | 26.8 ± 3.07 | 92.80 ± 8.03 | 116.0 ± 10.55 | 89.0 ± 7.23 | 1.62 ± 0.4 | |
| | 7 | 30.83 ± 2.15 | 25.40 ± 2.17 | 102.0 ± 8.89 | 112.31 ± 10.86 | 93.7 ± 7.64 | 5.1 ± 1.08 | |
| GSSG | 0 | 23.5 ± 4.22 | 12.8 ± 1.95 | 102.0 ± 12.8 | 134. ± 9.8 | 90.03 ± 8.07 | 0.48 ± 0.032 | 11.0 ± 0.44* |
| | 3 | 62.3 ± 9.15 | 64.6 ± 7.13 | 280.0* ± 31.2 | 460. ± 40.8 | 306. ± 24.4 | 3.7* ± 0.32 | |
| | 7 | 147.0 ± 17.30 | 128.10 ± 16.55 | 624.0* ± 45.6 | 1024. ± 97.0 | 560. ± 48.8 | 15.2* ± 0.16 | |
| GSSG + 0.003% H₂O₂ | 0 | 17.4 ± 2.4 | 9.41 ± 2.02 | 90.8 ± 10.10 | 101.0 ± 9.88 | 73.5 ± 5.17 | 0.39 ± 0.11 | 11.6 ± 0.53* |
| | 3 | 109.6 ± 14.4 | 104.8 ± 15.30 | 314.0 ± 37.2 | 255.0 ± 22.3 | 355.* ± 36.2 | 2.93* ± 0.33 | |
| | 7 | 142.6 ± 16.3 | 174.0 ± 20.9 | 501.0* ± 48.3 | 1505 ± 131.0 | 890.* ± 78.3 | 13.6* ± 0.64 | |
| GSSG + 0.1% inosine | 0 | 28.7 ± 3.05 | 7.13 ± 0.98 | 129.8 ± 14.0 | 123.4 ± 10.01 | 109.0 ± 11.2 | 0.56 ± 0.16 | 12.7 ± 0.51* |
| | 3 | 75.0 ± 8.13 | 36.4 ± 4.8 | 618.0* ± 52.3 | 693.0* ± 61.8 | 517.* ± 44.5 | 1.64* ± 0.19 | |
| | 7 | 210.4 ± 26.8 | 84.0 ± 10.03 | 520.0* ± 51.0 | 1810.* ± 129. | 2120.* ± 193. | 5.15* ± 0.59 | |
| GSSG + 0.1% cystamine | 0 | 20.8 ± 2.91 | 16.7 ± 1.88 | 118.9 ± 12.3 | 114.6 ± 9.87 | 95.6 ± 9.1 | 0.61 ± 0.15 | 12.5 ± 0.56* |
| | 3 | 109.2 ± 10.45 | 37.03 ± 4.15 | 156.6 ± 11.8 | 708.0* ± 61.9 | 326* ± 28.7 | 2.26* ± 0.17 | |
| | 7 | 168.0 ± 21.15 | 211.0 ± 25.6 | 414.0* ± 18.4 | 1950.* ± 180.0 | 785.* ± 69.0 | 6.08* ± 0.77 | |
| 0.003% H₂O₂ | 0 | 15.5 ± 2.04 | 14.95 ± 2.16 | 134.0 ± 15.6 | 129. ± 10.0 | 119. ± 9.13 | 0.63 ± 0.15 | 9.9 ± 0.24 |
| | 3 | 44.7 ± 6.14 | 22.0 ± 2.81 | 156.0 ± 16.3 | 205.8 ± 18.3 | 144.5 ± 12.8 | 5.4 ± 0.62 | |
| | 7 | 28.6 ± 4.11 | 40.8 ± 5.12 | 110.9 ± 12.5 | 190. ± 16.7 | 248. ± 20.7 | 20.3 ± 2.28 | |
| 0.1% inosine | 0 | 36.7 ± 5.12 | 16.50 ± 1.09 | 115.0 ± 12.5 | 81.4 ± 6.13 | 122.0 ± 10.0 | 0.58 ± 0.13 | 9.8 ± 0.21 |
| | 3 | 48.2 ± 7.13 | 20.19 ± 1.54 | 90.0 ± 7.11 | 105. ± 11.3 | 96.5 ± 8.7 | 6.8 ± 0.8 | |
| | 7 | 31.0 ± 5.12 | 13.40 ± 1.68 | 129.0 ± 10.4 | 184. ± 16.1 | 144.8 ± 12.9 | 25.0 ± 2.22 | |
| 0.1% cystamine | 0 | 30.0 ± 4.02 | 14.9 ± 2.05 | 72.7 ± 9.10 | 107 ± 8.06 | 80.5 ± 7.14 | 0.67 ± 0.22 | 9.93 ± 0.27 |
| | 3 | 41.5 ± 5.81 | 15.25 ± 1.80 | 184.0 ± 15.6 | 216. ± 19.08 | 204. ± 16.1 | 6.0 ± 0.49 | |
| | 7 | 22.3 ± 3.0 | 20.18 ± 2.50 | 170.6 ± 14.3 | 315. ± 9.80 | 220. ± 19.1 | 19.9 ± 1.67 | |

Differences are statistically significant (p < 0.05) as compared as compared to the control group Therefore, animal treatment according to present invention led to: significant increasing in endogenous production of cytokines and erythropoietin blood levels was observed in the majority of cases.

TABLE 15

Effect of GSSG administered intravenously on cytokine and erythropoietin serum levels in cancer patients

| Patients | Number of injections | Serum level, pg/mL | | | | |
|---|---|---|---|---|---|---|
| | | IL-1β | IL-6 | TNFα | INFα | erythropoietin |
| Pulmonary | 0 | 18.3 | 138.0 | 57.2 | 83.3 | 143.0 |
| adenocarcinoma with | 3 | 96.7 | 156.0 | 280.0 | 395.6 | 605.0 |
| pleural metastases | 7 | 104.6 | 150.0 | 315.0 | 378.0 | 548.0 |
| Stomach adenocarcinoma | 0 | 12.0 | 93.5 | 27.0 | 4.6 | 21.6 |
| with liver metastases | 3 | 28.1 | 228.0 | 215.0 | 33.6 | 53.5 |
| | 7 | 31.7 | 204.0 | 147.0 | 34.0 | 47.1 |
| Suprarenal corticocytoma | 0 | 8.4 | 61.9 | 39.8 | 41.3 | 8.3 |
| with liver, pulmonary and | 3 | 12.9 | 105.0 | 113.0 | 56.0 | 32.4 |
| peritoneal metastases | 7 | 17.3 | 167.0 | 103.9 | 61.5 | 28.6 | of IL-2, IL-6, IFNα and TNFα; and a reliable inhibition of progression of experimental tumors and prolongation of the mean survival time.

New properties of a previously known substance—oxidized glutathione (GSSG), and its pharmacologically active compositions, containing 0.003% hydrogen peroxide, or 0.1% of inosine, or 0.1% cystamine, found in the pre-clinical studies, are thought to be sufficient to declare that GSSG and its, pharmacological formulations possess an obvious biological and pharmacological activity, as well as a therapeutic effect. This justifies the application of the corresponding drug forms of GSSG along and GSSG in combination with pharmaceutically acceptable components capable of extending the oxidized glutathione half life, for preventing and treating the diseases in which stimulation of endogenous production of cytokines and hemopoietic factors is advantageous and considered beneficial by those who are skilled in the art.

The following examples (##6–12) of the GSSG drug forms clinical use support the idea of utilizing GSSG as an inducer of the endogenous cytokine and hemopoietic factor production in man, and provide for the method for disease treatment based on the above GSSG properties.

EXAMPLE #6

Effect of GSSG Drug Form on the Endogenous and Erythropoietin Production in Patients Having Neoplastic Disease Data presented in this example demonstrate the GSSG stimulatory effect on the endogenous cytokine and hemopoietic factor production in cancer patients. GSSG solution (5 mg/mL) was administered intravenously, slowly, every other day a 5 mg per injection. The cytokine endogenous production was determined by their blood levels prior to the first administration (with blood collected 24 hours before dosing) and after the third and the seventh injections. The cytokine levels were assessed by immunoenzyme technique using commercially available kits (Medgenix, Belgium), and expressed as pg/mL of culture medium.

As seen from the data given in Table 15, a pronounced stimulation of the endogenous cytokine (IL-1β, IL-6, TNF-α, IFN-α) and erythropoietin was noted as soon as after three first injections of GSSG. After the seventh administration (14 days of treatment) a manifold increase in the cytokines and erythropoietin blood levels was observed in the majority of cases.

EXAMPLE #7

Stimulation of the Endogenous and Erythropoietin Production in a Patient Suffering from Colorectal Cancer Complicated with Chemotherapy-Induced Hemodepression A 44-year old female patient was operated on for colorectal mass grown through the ovary and metastases in the mesenteric and omental lymph nodes ($T_4N_3M_1$). Postoperatively, 5-fluorouracil chemotherapy was conducted (total course dose 5.5 g) with resultant severe hemotoxicity.

One month after the chemotherapy the patient was reexamined, and ultrasonography of the peritoneum and computed tomography of the liver revealed an oval-shaped 13×10 mm solitary metastasis in the left liver lobe. Repeat blood counts showed incomplete recovery of the blood indices (leukopenia, lymphopenia, anemia, and thrombocytopenia of various severity were noted) rendering further chemotherapy impossible.

Laboratory parameters prior to the use of the oxidized glutathione drug form (5 mg of GSSG in 1 mL of 0.003% hydrogen peroxide) are listed in Table 6. The treatment according to the subject method was commenced with GSSG given intravenously for seven days, 5 mg once daily. After a 3-day interval, the treatment was resumed with 15 mg daily dose, IV, 10 days. This course was followed by a 7-day recess after which the therapy was continued with GSSG being given every other day IM, 15 mg daily (a total of 20 injections).

50 days following commencement of the treatment the patient was reevaluated, and ultrasonography of the peritoneum and computed tomography of the liver showed a considerable shrinkage (more than 50% of the pretreatment size) of the solitary hepatic metastasis. The post-treatment immunological indices are given in Table 16.

As seen from the data, both red and white blood cell counts have significantly improved, platelets almost completely recovered, ESR reduced, CD4+, CD8+, NK cell numbers increased. A considerable stimulation of the endogenous cytokine and erythropoietin production, with TNF (together with increased natural killers) being probably responsible for the regression of the hepatic metastasis. These changes were accompanied by an improved general condition of the patient.

This clinical case indicates apparent therapeutic efficacy of the subject method. The administered therapy resulted in significant stimulation of the endogenous cytokine and hemopoietic factor production, reduction in hepatic metastasis size, normalization of immunity parameters, and overall improvement in the patient's wellness.

TABLE 16

Effect of GSSG on blood indices, cytokine and erythropoietin serum levels, and immunological parameters in patient with colorectal cancer and chemotherapy induced hemodepression

| Parameter | Prior to the treatment | After the treatment completion |
|---|---|---|
| Erythrocytes | $2.9 \times 10^{12}$/L | $4.1 \times 10^{12}$/L |
| Hemoglobin | 79 g/L | 108 g/L |
| Leukocytes | $3.6 \times 10^9$/L | $5.4 \times 10^9$/L |
| Lymphocytes | $0.67 \times 10^9$/L | $1.57 \times 10^9$/L |
| Platelets | $92 \times 10^9$/L | $208 \times 10^9$/L |
| ESR | 44 mm/hr | 19 mm/hr |
| CD4+ | $204 \times 10^6$/L | $609 \times 10^6$/L |
| CD8+ | $255 \times 10^6$/L | $661 \times 10^6$/L |
| NK-cells | $39 \times 10^6$/L | $109 \times 10^6$/L |
| IL-1β | 203 pg/mL | 815 pg/mL |
| IL-6 | 318 pg/mL | 1014 pg/mL |
| TNFα | 117 pg/mL | 937 pg/mL |
| IFNγ | 84 pg/mL | 506 pg/mL |
| Erythropoietin | 162 pg/mL | 618 pg/mL |

EXAMPLE #8

Stimulation of the Endogenous Cytokine Production in an AIDS Patient with Cryptococcal Meningitis A 28-year old male was admitted with a previously confirmed diagnosis of AIDS, stage 3/4C (WHO staging system) in moderately grave condition. The patient presented with paroxysmal headache, dizziness, and vomiting. Weight 47 kg, Karnofsky score 60, torpid, fevers up to 39° C., dyspnea at rest.

Neurological examination revealed nuchal rigidity and diminished knee, ankle, biceps and triceps reflexes. Cerebrospinal fluid culture was positive for *Cryptococcus neoformans* which served the basis for making the diagnosis of cryptococcus meningoencephalitis, and the AIDS stage was refined as 4C.

A vigorous infusion therapy was started. In addition to palliative therapy the patient received a course of Fungizone (Amphotericin B) with no positive outcome. The neurologic symptomatology and the patient's general state continued to deteriorate. A low to moderate grade fever (37.5–38.5° C.) persisted.

By the time oxidized glutathione was started (5 mg/mL), the patient had a significant drop in CD4+ and CD8+ peripheral blood counts as well as anemia and overall lymphopenia (see Table 17).

The patient received the treatment to the subject method for 3 months (1 mL of the GSSG solution per administration). During the first month of treatment the patient was dosed every other day (first 10 days intravenously, the rest of the month—intramuscularly); during the second month the patient received the drug every three days (first 10 days IV, the rest of the month—subcutaneously).

By the middle of the first month therapy, the patient's condition improved significantly with the neurologic sign alleviated and low-grade fever not exceeding 37.5° C. In the course of treatment, the patient's cerebrospinal fluid was mycologically examined twice (cytology, cultures, latex-agglutination test for cryptococcal antigen). Towards the end of the first month therapy the number of viable *Cryptococcal neoformans* organisms was found to be considerably reduced. By the end of the second month the cytological, culture, and immunologic tests showed cerebrospinal fluid to be free of the pathogen. Because of the drastic improvement in the patient's state, during the third month the drug was given once weekly IM.

The hematology/immunology findings upon the therapy completion are given in Table 17. As evident from the table, the anemia signs have reduced and a significant increase in the number of lymphocytes and their subsets has taken place. These findings constitute AIDS restaging from 4C to 4B.

Noteworthy is the sizable elevation of the cytokine blood levels, with IL-2, IL-6, and IFN-γ playing the key role in the host defense against pathogenic fungi.

At discharge, the patient's condition was found satisfactory with body weight being 60 kg (weight gain made up 21.7% of the admission), normal body temperature, Karnofsky score of 90, and no neurological signs.

TABLE 17

Effect of GSSG on blood indices, cytokine and erythropoietin serum levels, and immunological parameters in patient with AIDS and cryptococcal meningitis

| Parameter | Pre-treatment | Post-treatment |
|---|---|---|
| Erythrocytes | $3.1 \times 10^{12}$/L; | $3.9 \times 10^{12}$/L; |
| Hemoglobin | 84 g/L; | 126 g/L; |
| Leukocytes | $6.3 \times 10^9$/L; | $5.1 \times 10^9$/L; |
| Lymphocytes | $0.8 \times 10^9$/L; | $1.45 \times 10^9$/L; |
| CD4+ | $55 \times 10^6$/L; | $338.3 \times 10^6$/L; |
| CD8+ | $135 \times 10^6$/L; | $883 \times 10^6$/L; |
| IL-1β | 18.9 pg/mL; | 123.4 pg/mL; |
| IL-2 | 0.32 IU/mL | 3.7 IU/mL |
| IL-6 | 16.0 pg/mL; | 272.0 pg/mL; |
| IL-10 | 45.0 pg/mL; | 608.0 pg/mL; |
| IFNα | 27.0 pg/mL. | 314.0 pg/mL. |
| IFNγ | 15.7 pg/mL | 349.8 pg/mL |

EXAMPLE #9

Stimulation of the Endogenous Cytokine Production and Therapeutic Effect in Patients with AIDS Complicated by Isosporiasis A 38-year old male had been observed for 2 years with the diagnosis of AIDS, stage 3C (WHO Staging System). During the preceding year, recurrent episodes of oral and esophageal candidiasis had been recorded as well as chronic intestinal isosporiasis manifested by poor appetite, nausea, frequent vomiting and watery stools containing blood and mucus. Repeatedly used clotrimoxazole (trimethoprim plus sulfamethoxazole, TMP-SMX) had produced unsteady remissions with rapid recurrence of the symptomatology. During the last month prior to admission another relapse of isosporiasis had occurred. The treatment with clotrimoxazole, immodium (loperamide) had brought no relief. The patient's condition had been gradually deteriorating: refractory fever 38° C. and above, 6–7 loose bloody and mucous stools a day, vomiting, advancing weight loss (15% of the premorbid weight in one year). The patient had been admitted with progressive worsening of his condition.

On admission, the patient presented with moderately grave condition, Karnofsky score of 50, fever 38.2° C., emaciation (body weight 42 kg), virtually total lack of subcutaneous fat, pallor of skin, the signs of oral and esophageal candidiasis. Stool examination revealed a large number of *Isospora belli* oocysts.

By the time the therapy according to the subject method was started, the patient had lymphopenia, marked decline in CD4+ and CD8+ lymphocytes, hypoproteinemia (see Table 18).

The patient received the oxidized glutathione drug form (5 mg of GSSG in 1 mL 0.003% hydrogen peroxide) for 2 months (1 mL of the GSSG solution per administration). During the first month of treatment the patient was dosed every other day (first 10 days intravenously, the rest of the month—intramuscularly); during the second month the patient received the drug every three days (first 10 days IV, the rest of the month—subcutaneously).

The patient's condition began to noticeably improve after the first two weeks of treatment. By the end of the first month therapy the patient moved bowels no more than 1 or 2 times a day with stools being blood-free; body temperature only occasionally exceeded 37° C. At the end of the second month stool reexamination showed feces to be negative for *Isospora belli*. Because of the drastic improvement in the patient's state, during the third month the drug was given prophylactically once weekly IM. No relapses of the disease were noted.

The findings of hematology/blood chemistry evaluations upon the therapy completion are given in Table 18. As seen from the table, hypoproteinemia has reduced, the number of lymphocytes and their subsets considerably increased with the resultant restaging of AIDS to 3B stage according to the WHO Staging System.

Noteworthy is the marked increase of the cytokine blood levels, with IL-2 and IFN-γ known to play an important part in the host defense against protozoan infections.

As a result of the therapy administered the patient's condition improved drastically, fatigue alleviated, appetite regained. The weight gain comprised 30% of the admission value, Karnofsky score—90. On physical examination the patient's condition was rated as satisfactory. During 1.5 month follow-up no diarrhea relapses were reported.

TABLE 18

Effect of GSSG on blood indices, cytokine and erythropoietin serum levels, and immunological parameters in patient with AIDS and isosporiasis

| Parameter | Pre-treatment | Post-treatment |
| --- | --- | --- |
| Erythrocytes | $4.04 \times 10^{12}$/L | $4.75 \times 10^{12}$/L |
| Hemoglobin | 108 g/L | 129 g/L |
| Leukocytes | $5.4 \times 10^9$/L | $6.0 \times 10^9$/L |
| Lymphocytes | $0.9 \times 10^9$/L | $1.8 \times 10^9$/L |
| CD4+ | $125 \times 10^6$/L | $436.5 \times 10^6$/L |
| CD8+ | $270 \times 10^6$/L | $949.3 \times 10^6$/L |
| Total protein | 46 g/L | 78 g/L |
| IL-1β | 27.8 pg/mL | 202.4 pg/mL |
| IL-2 | 0.51 IU/ml | 12.9 IU/ml |
| IL-6 | 13.5 pg/mL | 348.0 pg/mL |
| IL-10 | 62.0 pg/mL | 956.0 pg/mL |
| IFNα | 148.3 pg/mL | 860.0 pg/mL |
| IFNγ | 61.2 pg/mL | 698.8 pg/mL |

EXAMPLE #10

Stimulation of the Endogenous Erythropoietin Production and Therapeutic Effect in Patient with Hypoplastic Anemia and Pancytopenia A 37-year old male had been observed for about a year with anemia of unknown origin the severity of which had been gradually building up. For 10 months he had been troubled with fatigability, dizziness, frequent nasal bleedings, unusual susceptibility to respiratory infections, three episodes of pneumonia with one of them being croupous pneumonia. During the year the patient had lost 10% of his usual weight. Repeated outpatient treatment with oral and intravenous iron preparation, folic acid, B vitamins, including $B_{12}$, had produced no effect. One admission the patient presented with moderately grave condition, dyspnea on moderate exertion, bruises, and isolated petechial spots. Successive hematology analyses have revealed moderately severe to severe fairly hypochromic (color index 0.7–0.9) normocytic anemia ($1.5-2.5 \times 10_{12}$/L), anisocytosis and poikilocytosis, moderate leukopenia, and thrombocytopenia within $50-80 \times 10^9$/L.

An aggressive infusion therapy with iron preparations, folic acid, cyanocobalamin, vitamins, prednisone, and repeated erythrocyte transfusions resulted in only marginal relief.

Bone marrow differential (punch biopsy) revealed marked hypocellularity with medullary cavities populated predominantly with fat cells. Both myeloid and erythroid lineages are significantly suppressed with the erythroid/myeloid ration noticeably diminished. Megakaryocytes are scant in number with relative increase in nondifferentiated cells, plasma cells, and blasts. Iron stores are enriched. Diagnosis: hypoplastic anemia of unknown origin, pancytopenia.

Complete blood count and erythropoietin levels by the time the oxidized glutathione drug form (5 mg GSSG in 1 mL of 0.003% hydrogen peroxide) was started are given in Table 9. As is evident from the table, the laboratory findings are consistent with those characteristic of hypoplastic anemia with no typical increase of erythropoietin blood level, however. Moreover, the erythropoietin level was found to be considerably below the lower normal limit (9.2 pg/mL with the reference range 30–170 pg/mL corresponding to 3–17 mIU/mL).

The oxidized glutathione formulation therapy was started with intramuscular injections of 1 mg GSSG b.i.d. for three days. Further the dose was escalated up to 5 mg b.i.d. for 7 days. Blood counts have shown less severe anemia. From that point, the drug form was dosed at 10 mg IM once daily for 10 days and then, the RBC counts steadily recovering, the therapy was switched to IV administration of GSSG, once every three days for 30 days. Vitamins and iron preparations were given concomitantly per os.

Hematology findings obtained 50 days following the subject treatment onset are listed in Table #19. Both RBS and WBC counts significantly improved, as did the platelet counts, ESR reduced, erythropoietin levels exceeded the upper normal limit. Clinically, fatigue, dizziness, and dyspnea disappeared. On examination, no petechial spots or bruises could be found with no nasal bleedings observed or reported. The weight gain made up 5.5 kg (8% of the premorbid weight).

Bone marrow reexamination (punch biopsy upon therapy completion) found the myeloid tissue to occupy 60% of the medullary cavities with erythroid/myeloid ratio in the myeloid tissue isles exceeding the norm. There were normoblastoid hyperplasia signs with megaloblastoid cells found in normoblast congregations. Mast cells were encountered, megakaryocytes were present in abundance. Iron stores appeared to be somewhat enriched.

This clinical case indicates a clear therapeutic efficacy of the drug form. Due to the treatment administered the initially suppressed endogenous erythropoietin production received a potent boost. As a result, the hematology parameters virtually recovered and the anemia clinical signs resolved. The patient was discharged in satisfactory condition.

TABLE 19

Parameters

Erythrocytes
Hemoglobin
Color index
Reticulocytes
Leukocytes
Lymphocytes
Platelets
ESR
Erythropoietin

EXAMPLE #11

Stimulation of Endogenous Cytokine Production and the Therapeutic Effect in a Patient with a Stomach Cancer, Peritoneal Metastases, Ascites, Plenomegaly and Cholestatic Hepatitis A 33-year old patient was diagnosed as having stomach neoplasm for more than 2 years (adenocarcinoma of moderate differentiation degree). In 1993, the patient was operated on for a malignant stomach ulcer; and numerous dense lymph nodes were found in the *porte hepatis* which were considered to be metastases.

In January 1994 the course of chemotherapy (5FU) was complicated by the severe cholestasis and percutaneous drainage of the left and right liver ducts was undertaken, that 6 month's later was followed by the choledochoejunostomy with changeable transliver drains with Brown's anastomosis.

In November 1995 the state of the patient worsened. According to the examinations the patient experienced an active secondary hepatitis. The liver was enlarged and painful and protruded from the costal arch up to 5–6 sm. Blood chemistry indices proved to be persistently abnormal: bilirubin—40.0 due to indirect (up to 31.0); activity of amino transferases—approximately 6 times higher than upper normal limit, hypoalbunemia was up to 26%; and there was also hypergammaglobulinemia; hypercholesterolemia was up to 10.2 μmol/l.

During fibrogastrocopy (November, 1995), a tumor of the stomach located in the middle area of the stomach body and extending about 8 cm was confirmed. The tumor was solid-like. Stomach walls were rigid. Histology examination defined the tumor as adenocarcinoma of moderate degree laparotomy. Ascites were found with plural metastases all over the peritoneum, splenomegaly. The patient was identified as inoperable.

A decision was taken to apply GSSG drug form containing 0.1% inosine. The drug was injected parenterally (intramuscular and intravenous), and additionally, the drug form was used via local injections around the tumor tissue with the help of endoscope. An average dose which was used for intramuscular and intravenous injections—0.1–0.5 mg/kg, and for local injections—up to 50 mg in situ. Parenteral injections of the drug were applied every other day, b.i.d. (intravenous injections at the morning, and intramuscular ones—at the evening), during three weeks, and after that—two times in a week, during four weeks. Two months after the beginning of the treatment with the drug form used fibrogastroduodenoscopy showed that esophagus was passable, mucous membrane was pink, cardia rosette was partly closed. On an empty stomach, a moderate amount of foamy secretion was in the stomach, which was intensively colored with bile. The tumor extent was 5 cm. At the same time, substantial improvement of hematology and blood chemistry indices were found.

Four month's later, the liver protruded 1 cm beyond the rib arch. On palpation the liver was not painful. Supersonic examination showed the appearance of fibrous tissue instead on the place of some areas previously affected with tumor tissue. Fibrogastroduodenoscopy performed in May, 1996, showed that the esophagus was partly closed. There was light turbid liquid in the stomach, which contained saliva. Mucous membrane was pink. The tumor was 3.6 cm in extent with the stomach walls being elastic. Duodenum was passable.

By comparison with results of examination conducted before treatment with the use of the GSSG drug form mentioned (November, 1995) the tumor was shrunk in its extent for 55%. Simultaneously there were significant beneficial changes in hepatic tests, hematology and immunology indices (see table 20).

Thus, the treatment according to the present invention resulted in partial regress of neoplastic process with simultaneous obvious beneficial changes in hematology, blood chemistry and immunology parameters, and significant improvement of life quality.

TABLE 20

Effect of Glutamed MF-R-30 on blood and immunology indices and cytokine levels in patient with stomach cancer, peritoneal metastases, ascites and splenomegly.

| Parameter | Prior to the treatment | 2 months after the treatment beginning | 4 months after the treatment beginning |
|---|---|---|---|
| Erythrocytes, $10^{12}$/L | 3.2 | 3.7 | 4.4 |
| Hemoglobin, g/L | 112 | 121 | 135 |
| Platelets, $10^9$/L | 205 | 195 | 275 |
| Leukocytes, $10^9$/L | 12.4 | 8 9 | 8.1 |
| Neutrophils (stab), % | 12 | 8 | 2 |
| Neutrophils (segm.), % | 54 | 44 | 47 |
| Lymphocytes, % | 21 | 36 | 41 |
| Monocytes, % | 8 | 7 | 9 |
| Eosinophils, % | 5 | 4 | 1 |
| ESR, mm/hr | 54 | 15 | 8 |
| Total protein, g/L | 62 | 76 | 82 |
| Albumin, % | 26 | 45 | 47 |
| α1-globulin, % | 3.0 | 7 | 11 |
| α2-globulin, % | 14.0 | 12 | 7 |
| β-globulin, % | 7 | 10 | 13 |
| γ-globulin, % | 50 | 26 | 22 |
| A/G ratio | 0.35 | 0.82 | 0 9 |
| Urea, mmol/L | 6.6 | 6.1 | 7.4 |
| Creatinin, mmol/L | 0.11 | 0.09 | 0.82 |
| Bilirubin, mcmol/L | 40.0 | 32.4 | 20.1 |
| Bilirubin conjugated, mcmol/L | 31.0 | 21.4 | |
| Prothrombin index, % | 75 | 79 | 95 |
| Glucose, mmol/L | 5.9 | 5.3 | 4.2 |
| SGOT, mmol/hr/L | 4.4 | 1.21 | 0.21 |
| SGPT, mmol/hr/L | 3.8 | 1.21 | 0.17 |
| Lymphocytes, $10^6$/L | 260.4 | 3204 | 3321 |
| B-lymphocytes (CD20$^+$) $10^6$/L | 26 | 192 | 368 |
| CD4$^+$-lymphocytes, $10^6$/L | 132.8 | 574 | 1024 |
| CD8$^+$-lymphocytes, $10^6$/L | 13 | 374 | 908 |
| CD4$^+$/CD8$^+$ | 10.2 | 1.5 | 1.1 |
| IL2-receptor bearing cells (CD25$^+$), $10^6$/L | 26.8 | 498 | 2009 |
| HLA11-receptor bearing cells, $10^6$/L | 13 | 258 | 754 |
| NK-cells (CD16$^+$), $10^6$/L | 26 | 324 | 576 |
| IgA, g/L | 3.2 | 2.38 | 2.38 |

TABLE 20-continued

Effect of Glutamed MF-R-30 on blood and immunology indices and cytokine levels in patient with stomach cancer, peritoneal metastases, ascites and splenomegly.

| Parameter | Prior to the treatment | 2 months after the treatment beginning | 4 months after the treatment beginning |
|---|---|---|---|
| IgM, g/L | 3.6 | 0.58 | 1.42 |
| IgG, g/L | 21.82 | 14.34 | 12.2 |
| Immune Complexes, OD units | 337 | 216 | 117 |
| IL-1β, pg./mL | 92 | 727 | 813 |
| IL-2, IU/mL | 4.05 | 41.0 | 47.3 |
| IL-6, pg./mL | 118 | 806 | 551 |
| IFNα, pg./mL | 70.8 | 672 | 604 |
| IFNγ, pg./mL | 105 | 624 | 519 |
| TNF, pg./mL | 183 | 707 | 980 |

EXAMPLE #12

Stimulation of Endogenous Cytokine Production and the Therapeutic Effect in a Patient with Skin Cancer (Merkel's Cell Carcinoma), Local Lymph Node Metastases and Chemotherapy-Hemo- and Induced Immunodepression A male patient, 64 years old, has been under medical supervision since August, 1995, when a hyperemic painless mass appeared in the scapular area, which had progressively grown in size. After a month's time, the mass spread over the axillary space, kept increasing, and became painful. A fever appeared (38.9° C.). Histological and immunological examination in October, 1995 made the diagnosis clear: neuroendocrinal form of skin cancer (Merkel's cell carcinoma) stage III.

In December, 1995 the patient was given a course of CMF chemotherapy (cyclophosphamide+methotrexate+fluorouracil) without appreciable curative effect. At the same time an obvious hemopoiesis depression (leukocytes 2.4×$10^9$/L) developed with simultaneous growth of cervical and superclavicular lymph nodes associated with local skin hyperemia.

In January–February 1996 chemotherapy scheme was changed: cysplatine+cyclophosphamide (CP instead of CMF). The chemotherapy brought about the following complications—cytopenia (leukocytes—1.4×$10^9$/1), cardiotoxicity in the form of ischemia deterioration. After the 2nd course of chemotherapy a substantial tumor progression was observed: necrosis in the left subaxillary area with fistula formation; edema of the left arm; infiltrating growth into soft tissues in the area of the left shoulder and the left subaxillary tissues; intoxication; persistent fever (38.8° C.). Because of inefficacy of chemotherapy and the obvious progression of the process, it was decided to administer a course of GSSG drug form in combination with 0.1% cystamine, together with chemotherapy (CMF).

After 10 daily injections of the GSSG drug form used (intravenously and intramuscularly, the dose 0.1–0.5 mg/kg per an injection), it was noticed: the following changes in the patient's status was revealed: improved quality of life (good appetite, mobility); ulceration drying out, abolition of suppurative discharge; fistula scarring, 30% tumor shrinkage; normal body temperature; limitation of hyperemic areas, the improvement of hematology indices.

The 3rd and 4th courses of chemotherapy (CMF) were carried out together with GSSG drug form (intravenous and intramuscular injections, b.i.d., intravenous dose 0.5 mg/kg; and intramuscular dose 0.2 mg/kg). Parenteral administration of the preparation was 3 times in a week, with local injections in the two spots around the tumor through the endoscope once a week (up to 25 mg for each spot). The following results were obtained: tumor process regression; good endurance of chemotherapy, the disappearance of pain syndrome, constant improvement of life quality, restoration of immunity and hemopoiesis, increasing level of cytokines and hemopoietic factors (see table 21).

In two months the treatment with the use of the present invention there was a stable level of endogenous production of cytokines and hemopoietic factors; the diminution of the left cervical and supraclavicular lymph nodes; the 70% shrinkage of tumor size in two dimensions; positive shifts in immunology indices; lack of chemotherapy hemodepression.

The clinical observation proves the clear curative effect of the treatment according to the present invention: together with the obvious stimulation of endogenous production of cytokines and hemopoietic factors there were a substantial decrease in tumor size, improvement of life quality, and beneficial changes in hematology, blood chemistry and immunology parameters.

TABLE 21

Effect of GSSG on blood and immunology indices and cytokine levels in patient with skin cancer (Merkel's cell carcinoma), local lymph node metastases and chemotherapy-induced hemo- and immunodepression.

| Parameter | Prior to the treatment | 3 months after the treatment beginning |
|---|---|---|
| Erythrocytes, $10^{12}$/L | 3,9 | 4,1 |
| Hemoglobin, g/L | 112 | 114 |
| Platelets, $10^9$/L | 210 | 262 |
| Leukocytes, $10^9$/L | 2.4 | 7.2 |
| Neutrophils (stab), % | 6 | 8 |
| Neutrophils (segm.), % | 79 | 60 |
| Lymphocytes, % | 8 | 24 |
| Monocytes, % | 4 | 7 |
| Eosinophils, % | 3 | 1 |
| ESR, mm/hr | 43 | 13 |
| Total protein, g/L | 61 | 78 |
| α1-globulin, % | 9.20 | 2.3 |
| α2-globulin, % | 12.32 | 8.2 |
| β-globulin, % | 13.08 | 14.0 |
| γ-globulin, % | 21.69 | 18.8 |
| A/G ratio | 0.78 | 0.94 |
| Urea, mmol/L | 8.54 | 4.3 |
| Creatinin, mmol/L | 0.123 | 0.095 |
| Bilirubin, mcmol/L | 4.6 | 4.1 |
| Prothrombin index, % | 82 | 100 |
| Glucose, mmol/L | 5.5 | 4.3 |
| SGOT, mmol/hr/L | 0.48 | 0.32 |
| SGPT, mmol/hr/L | 0.43 | 0.21 |
| Lymphocytes, $10^6$/L | 192 | 1728 |
| B-lymphocytes (CD20$^+$) $10^6$/L | 60 | 234 |
| CD4$^+$-lymphocytes, $10^6$/L | 84 | 604 |
| CD8$^+$-lymphocytes, $10^6$/L | 13 | 329 |
| CD4$^+$/CD8$^+$ | 6.5 | 1.8 |
| IL2-receptor bearing cells (CD25$^+$), $10^6$/L | 64 | 881 |
| HLA11-receptor bearing cells, $10^6$/L | 36 | 498 |
| NK-cells (CD16$^+$), $10^6$/L | 24 | 624 |
| IgA, g/L | 4.9 | 5.2 |
| IgM, g/L | 0.99 | 1.24 |
| IgG, g/L | 24.3 | 15.6 |
| Immune Complexes, OD units | 264 | 111 |
| IL-1β, pg./mL | 156 | 637 |
| IL-2, IU/mL | 1.12 | 36.5 |
| IL-6, pg./mL | 244 | 1029 |
| IFNα, pg./mL | 79 | 513 |

TABLE 21-continued

Effect of GSSG on blood and immunology indices and cytokine levels in patient with skin cancer (Merkel's cell carcinoma), local lymph node metastases and chemotherapy-induced hemo- and immunodepression.

| Parameter | Prior to the treatment | 3 months after the treatment beginning |
|---|---|---|
| IFNγ, pg./mL | 58 | 234 |
| TNF, pg./mL | 202 | 855 |

While specific embodiments of the invention have been shown and described, many modifications are possible. For example, other ingredients which do not affect the action of GSSG and/or its enhancers may be intermixed with GSSG alone or in combination with its extenders for application to the body. The dosage forms can be packaged in kit form along with syringe or applicator of any type. Preferably instructions for application to specific diseases are included in any kit, including the therapeutic agent. We indicate below preferred applications of GSSG with or without extenders in doses from 0.01 to 2 mg per kg of body weight for one or more days intravenously, intramuscularly or intralymphatically for up to 6 months as has been found effective for the diseases noted:

A prophylactic, therapeutic use of the methods and therapeutic agents of this invention can be made for immunodeficiency states where individuals have been exposed to radioactive and chemical affliction in cases of accidents such as nuclear or chemical disasters.

Where the various extenders have been noted, other specific extenders which prolong the half life of the oxidized glutathione may be used. In some cases, one or more of the different extenders can be used in combination.

While the drug for parenteral use is preferably in solution form, in some cases colloidal suspensions and the like can be used. Similarly, topical application can include the use of pharmaceutically acceptable ointments, creams and other bases such as petrolatum, lanolin or spermaceti bases which do not interact with the GSSH. Such base materials are known in the art. For topical application we lay out usage of any ointment base (petrolatum, lanolin or spermaceti) with addition of acetylsalicylique acid or acetylsalicylic acid.

Infectious and Immunopathology Diseases

AIDS: dosage rate—from 5 to 30 mg per day, entire course is of 6 month duration, with 2 week break after each month;
- the administration regimen during the first week—a single injection daily, alternating regimen: one day—intravenous injection, every other day—intramuscular injection;
- during the second week—twice a day: one time intravenously (in the morning), other time intramuscularly (in the evening);
- the third and the forth weeks—three times a week: $1^{st}$ time—intravenous injection, $2^{nd}$ and $3^{rd}$ time—intramuscular injection;

In case of encephalopathy it is recommended lumbar injections of the medicine once a week during three weeks.

Hepatitis: dosage rate—from 5 to 10 mg per day, entire course is from 1 to 2 months;
- during the first three weeks—a single injection daily, alternating regimen: one day—intravenous injection, every other day—intramuscular injection;
- afterwards:—two or three injections per a week, $_1$st time—intravenous injection, $_2$nd and $_3$rd time—intramuscular injection;

Herpes: the medicine administration course is the same as in hepatitis.

Tuberculosis: Inactive phase: dosage rate—from 5 to 10 mg per day, entire course is of 6 months, with 2 week break after each month and 1 month break after the 3 months of the medicine administration.
- during the first three weeks—a single injection daily, alternating regimen: one day—intravenous injection, every other day—intramuscular injection;
- during the forth week—two or three injections per a week, $_1$st time—intravenous injection, $_2$nd and $_3$rd time—intramuscular injection;

Active phase: dosage rate—from 5 to 10 mg per day, entire course is of 6 months, the administration regimen in an active phase is the same as in inactive phase.

Meningitis: dosage rate—from 5 to 90 mg per day, entire course is of 2 months;
- during the first two weeks—twice a day: one time intravenously (in the morning), other time intramuscularly (in the evening);
- afterwards:—two or three injections per a week, $1^{st}$ time—intravenous injection, $_2$nd and $_3$rd time—intramuscular injection;

Lumbar injections of the medicine—a single injection daily is recommended during three days.

Peritonitis: the medicine administration course is the same as in meningitis (except for lumbar injections).

Sepsis: dosage rate—from 5 to 60 mg per day, entire course is no less than 1 months up to full normalization of clinical state and blood data;
- during the first two or tree weeks—twice a day: one time intravenously (in the morning), other time intramuscularly (in the evening);
- afterwards:—two or three injections per a week, st time—intravenous injection, $_2$nd and $_3$rd time—intramuscular injection;

Purulent post-operative infectious complications—the medicine administration course is the same as in sepsis.

Immunodepression: dosage rate—from 5 to 20 mg per day, entire course is of 6 months, with 2 week break after each month;
- during the first three weeks—a single injection daily, alternating regimen: one day—intravenous injection, every other day—intramuscular injection;
- during the forth week—two or three injections per a week, 11 time—intravenous injection, $_2$nd and $_3$rd time—intramuscular injection;

Immunodeficiencies of infectious, radiation, or toxic origin: dosage rate is from 5 to 30 mg per day; the medicine administration course is the same as in immunodepression.

Multiple sclerosis: dosage rate is from 5 to 20 mg per day, entire course is of 3 months with 2 week break after each month, and after 6 month break—the repeating of entire course;
- the 1st month of the entire course: a single injection daily, alternating regimen: one day—intravenous injection, every other day—intramuscular injection;
- the $_2$nd month of the entire course: three injections per a week, 1st time—intravenous injection, 2nd and 3rd time—intramuscular injection;
- the 3rd month of the entire course: two intramuscular injections per a week, with dosage rate from 5 to 10 mg.

Neurodegenerative diseases: the medicine administration course is the same as in multiple sclerosis.

Alzheimer's sclerosis: the medicine administration course is the same as in multiple sclerosis.

Amyotrophic lateral sclerosis: the medicine administration course is the same as in multiple sclerosis.

Glomerulonephritis: dosage rate is from 5 to 30 mg per day, entire course is from 1 to 3 months with 2 week break after each month;
- during the first two weeks—a single injection daily, alternating regimen: one day—intravenous injection, every other day—intramuscular injection;
- afterwards:—two or three injections per a week, $1^{st}$ time—intravenous injection, $_2$nd and $_3$rd time—intramuscular injection;

Collagenoses:—the medicine administration course is the same as in glomerulonephritis.

Rheumatoid arthritis:—the medicine administration course is the same as in Glomerulonephritis.

Systemic lupus erythematosus:—the medicine administration course is the same as in Glomerulonephritis.

Allergic diseases:—the medicine administration course is the same as in Glomerulonephritis, along with the topical application of ointment (1–3% containing the active compound)—during 2 weeks, a single application per day, afterwards:—two applications per a week.

Psoriasis:—the medicine administration course is the same as in Glomerulonephritis, along with the topical application of ointment (1–3% containing of the active compound)—during 2 weeks, a single application per day, afterwards:—two applications per a week.

Neoplasms: dosage rate is from 5 to 90 mg per day, entire course is from 1 to 6 months with 2–4 week break after each month;
- a single injection daily, alternating regimen: one day—intravenous injection, every other day—intramuscular injection, without or along with endolymphatic application (dosage rate—from 30–90 mg per day) during 10 days, and local application (regional perfusion) by catheterization (dosage rate—from 30–90 mg per day) during 7 days, three or four applications per week;
- the treatment scheme is recommended along with polychemiotherapeutic treatment.

Metastatic processes and hemoblastoses: dosage rate is from 5 to 90 mg per day, entire course is from 1 to 6 months with 2–4 week break after each month;
- a single injection daily, alternating regimen: one day—intravenous injection, every other day—intramuscular injection, along with local application (regional perfusion) by catheterization (dosage rate—from 30–90 mg per day) during 7 days, three or four applications per week.

Lympho proliferative diseases (Lymphogranulomatosis and Lymphoma): dosage rate is from 5 to 90 mg per day, entire course is from 1 to 6 months with 2–4 week break after each month;
- during the first three weeks—a single injection daily, alternating regimen: one day—intravenous injection, every other day—intramuscular injection, along with endolymphatic application (dosage rate—from 30–90 mg per day) during first 10 days;
- afterwards:—the same treatment scheme in combination with glucocorticoides and cytostatics.

[1] Holmlund J. T. Cytokines. Cancer Chemother Biol Response Modif. 1993. 14P 150–206.

[2] Hansson M., Soderstrom T. The colony stimulating factors. Med Oncol Tumor Pharmacother. 1993. 10(1–2). P 5–12.

[3] Dillman R. O. The clinical experience with interleukin-2 in cancer therapy. Cancer Biother. 1994 Fall. 9(3). P 183–209.

[4] Whittington R., Faulds D. Interleukin-2. A review of its pharmacological properties and therapeutic use in patients with cancer. Drugs. 1993 Sep. 46(3). P 446–514.

[5] Hieber U., Heim M. E. Tumor necrosis factor for the treatment of malignancies. Oncology. 1994 Mar–Apr. 51(2). P 142–53.

[6] Morstyn G., Sheridan W. P. Hematopoietic growth factors in cancer chemotherapy. Cancer Chemother Biol Response Modif. 1993. 14P 353–70.

[7] Neidhart J. A. Hematopoietic cytokines. Current use in cancer therapy. Cancer. 1993 Dec 1. 72(11 Suppl). P 3381–6.

[8] Murray H. W. Interferon-gamma and host antimicrobial defense: current and future clinical applications. Am J Med. 1994 Nov. 97(5). P 459–67.

[9] Cirelli R. Tyring S. K. Interferons in human papillomavirus infections. Antiviral Res. 1994 Jul. 24(2–3). P 191–204.

[10] Sher A., Coffman R. L. Regulation of immunity to parasites by T-cells and T-cell derived cytokines. Annu. Rev. Immunol., 1992, 10, P. 385–409.

[11] Gillan E., Plunkett M., Cairo M. S. Colony-stimulating factors in the modulation of sepsis. New Horiz. 1993 Feb. 1(1). P 96–109.

[12] Nelson S. Role of granulocyte colony-stimulating factor in the immune response to acute bacterial infection in the nonneutropenic host: an overview. Clin Infect Dis. 1994 Feb. 18 Suppl 2P S197–204.

[13] Offenstadt G., Guidet B., Staikowsky F. Cytokines and severe infections. Pathol Biol (Paris). 1993 Oct. 41(8 Pt 2). P 820–31.

[14] Nemunaitis J. Use of hematopoietic growth factors in marrow transplantation. Curr Opin Oncol. 1994 Mar. 6(2). P 139–45.

[15] Mittelman M., Lessin L. S. Clinical application of recombinant erythropoietin in myelodysplasia. Hematol Oncol Clin North Am. 1994 Oct. 8(5). P 993–1009.

[16] Forman A. D. Neurologic complications of cytokine therapy. Oncology (Huntingt). 1994 Apr. 8(4). P 105–10; discussion 113, 116–7.

[17] Hack C. E., Ogilvie A. C., Eisele B., Eerenberg A. J., Wagstaff J., Thijs L. G. C1-inhibitor substitution therapy in septic shock and in the vascular leak syndrome induced by high doses of interleukin-2. Intensive Care Med. 1993. 19 Suppl 1P S19–28.

[18] Hieber U., Heim M. E. Tumor necrosis factor for the treatment of malignancies. Oncology. 1994 Mar–Apr. 51(2). P 142–53.

[19] Saito M. OK-432, a killed streptococcal preparation, in the treatment of animal and human cancer and its mechanisms of action. Forum on immunomodulators. Ed. Guenounou M. John Libbey Eurotext, Paris, 1995, P. 1–11.

[20] Barot-Ciorbaru R., Bona C. Immunomodulators from *Nocardia opaca*. Forum on immunomodulators. Ed. Guenounou M. John Libbey Eurotext, Paris, 1995, P. 1–11.

[21] Bioy C., Morales M., Guenounou M. RU 41740 (Biostim), an immunomodulating agent from bacterial origin. Ed. Guenounou M. John Libbey Eurotext, Paris, 1995, P. 1–11.

[22] Meister A. Anderson M. E. Glutathione. Annu. Rev. Biochem., 1983, 52:711–60.

[23] Beutler E. Nutritional and metabolic aspects of glutathione. Review. Annu. Rev. Nutr., 1989, 9:287.

[24] Textbook of biochemistry: with clinical correlations. Ed. Devlin T. M., 3rd ed. 1992, Wiley-Liss, Inc., NY. p. 522–525.

[25] Kehrer J. P., Lund L. G. Cellular reducing equivalents and oxidative stress. Free Radic Biol Med. 1994 Jul. 17(1). P 65–75.

[26] Michiels C., Raes M., Toussaint O., Remacle J. Importance of Se-glutathione peroxidase. catalase, and Cu/Zn-SOD for cell survival against oxidative stress. Free Radic Biol Med. 1994 Sep. 17(3). P 235–48.

[27] Cohen G. Enzymatic/nonenzymatic sources of oxyradicals and regulation of antioxidant defenses. Ann N Y Acad Sci. 1994 Nov 17, 738. P 8–14.

[28] Beckett G. J., Hayes J. D. Glutathine S-transferase: biomedical applications. Advan. Clin. Chem. 1993, vol. 30, P. 281–380.

[29] Composition and method for disease treatment. PCT/US/92/04653.

[30] Droge W., Schulze-Osthoff K., Mihm S., Galter D., Schenk H., Eck H. P., Roth S., Gmunder H. Functions of glutathione and glutathione disulfide in immunology and immunopathology. FASEB J. 1994 Nov. 8(14). P 1131–8.

[31] Sardesai V., M. Role of antioxidants in health maintenance. Nutr Clin Pract. 1995 Feb. 10(1). P 19–25.

[32] Giugliano D., Ceriello A., Paolisso G. Diabetes mellitus, hypertension, and cardiovascular disease: which role for oxidative stress? Metabolism. 1995 Mar. 44(3). P 363–8.

[33] Keusch G. T. Antioxidants in infection. J Nutr Sci Vitaminol (Tokyo). 1993. 39 SupplP S23–33.

[34] Dipeptide compound having pharmaceutical activity and compositions containing them. U.S. Pat. No. 4,761,399.

[35] g-L-Glutamyl-L-cysteine ethyl ester and pharmaceutical compositions containing the same as an effective ingredient. U.S. Pat. No. 4,927,808.

[36] Therapeutic agents for ischemic heart diseases. U.S. Pat. No. 4,968,671.

[37] Method for insuring adequate intracellular glutathione in tissue. EP 0 502 313 A2.

[38] Composition and method for disease treatment. PCT/US/92/04653.

[39] Glutathione as hemoprotective agent. PCT/EP/93/01494.

[40] Pharmaceutical compositions having antineoplastic activity. U.S. Pat. No. 4,871,528.

[41] Sokolovsky M., Wilchek M., Patchornik A. On the synthesis of cysteine peptides. J. Amer. Chem. Soc. 1964, Mar. 86(6), P 1202-6.

What is claimed is:

1. A method of stimulating endogenous production of cytokines and hemopoietic factors consisting essentially of introducing to a mammalian body in need of stimulation of cytokines or hemopoietic factors or both, an effective amount of oxidized glutathione, for a period of time to stimulate said endogenous production to obtain a predetermined, desired therapeutic effect.

2. A method in accordance with the method of claim 1, wherein said oxidized glutathione is introduced parenterally.

3. A method in accordance with the method of claim 1, wherein said oxidized glutathione is introduced either topically or locally.

4. A method in accordance with the method of claim 1, wherein said oxidized glutathione is introduced into said mammalian body along with an extender of the half life of said oxidized glutathione.

5. A method in accordance with the method of claim 4, wherein said extender is selected from the group consisting of pro-oxidant compounds, materials which are competitors of NADP.H-dependent reduction of GSSG into GSH catalyzed by glutathione reductase, compounds capable of producing reversible inhibition of reduction of NADP+ into NADP.H catalyzed by glucose-6-phosphate-dehydrogenose or by other NADP.H-dependent enzymes, and mixtures thereof.

6. A method in accordance with the method of claim 5, wherein said extender is hydrogen peroxide.

7. A method in accordance with the method of claim 5, wherein said extender is inosine.

8. A method in accordance with the method of claim 5, wherein said extender is cystamine.

9. A method in accordance with the method of claim 2, wherein said oxidized glutathione is introduced at a dose of from 0.01 to 0.5 mg per kilogram of body weight at least one time each 24 hour period until said desired therapeutic effect is obtained.

10. A method in accordance with the method of claim 9, wherein said oxidized glutathione is introduced parenterally in a pharmaceutically acceptable solution at a concentration of 0.01 to 2.0% by weight oxidized glutathione.

11. A method in accordance with the method of claim 10, wherein said solution further includes an extender selected from the group consisting of 0.03% to 0.0003% by weight hydrogen peroxide, 0.1% to 5% by weight inosine, 0.1% to 3% by weight cystamine, and mixtures thereof.

12. A method in accordance with the method of claim 1, wherein said mammalian body is in need of stimulation of cytokines or hemopoietic factors to treat a condition selected from the group consisting of neoplastic diseases, infectious diseases, hematologic diseases, and immunologic diseases.

13. A method in accordance with the method of claim 12, wherein said disease is infectious.

14. A method in accordance with the method of claim 12, wherein said disease is hematologic.

15. A method in accordance with the method of claim 12, wherein said disease is immunologic.

16. A method in accordance with the method of claim 12, wherein said disease is neoplastic.

17. A method in accordance with the method of claim 12, wherein said disease is selected from the group consisting of AIDS, hepatitis, herpes, tuberculosis, meningitis, peritonitis, sepsis, and purulent post-operative complications caused by infection.

18. A method in accordance with the method of claim 12, wherein said disease is selected from the group consisting of metastatic processes, hemoblastoses, malignant tumors, lymphogranulomatosis, lymphomas, immunodeficiencies caused by cancer and immunodepressions caused by radioactive or chemical affliction.

19. A method in accordance with the method of claim 1, 2, 3 or 4 wherein said oxidized glutathione is in a salt form.

20. A method in accordance with the method of claim 19, wherein said salt is the disodium salt.

21. A therapeutic agent for treating neoplastic, infectious, hematologic, immunologic and other diseases in which stimulation of the endogenous cytokines and hemopoietic factors production is considered beneficial, said therapeutic agent being in a dosage form for parenteral administration and consisting essentially of an effective amount of oxidized glutathione, a dimer of tripeptide γ-glutamyl-cysteinyl-glycine where two molecules of the tripeptide are linked via covalent disulfide bond between the cysteine residues, as an active substance, along with a pharmaceutically acceptable excipient, wherein said substance is formulated in the form of a sterile injectable solution of oxidized glutathione in a pharmaceutically acceptable solvent, and a pharmaceutically acceptable extender capable of enhancing and prolonging a therapeutic effect of said agent in the body of a user by increasing the half-life of oxidized glutathione, wherein said extender is hydrogen peroxide.

22. A therapeutic agent for treating neoplastic, infectious, hematologic, immunologic and other diseases in which stimulation of the endogenous cytokines and hemopoietic factors production is considered beneficial, said therapeutic agent being in a dosage form for parental administration and consisting essentially of an effective amount of oxidized glutathione, a dimer of tripeptide γ-glutamyl-cysteinyl-glycine where two molecules of the tripeptide are linked via covalent disulfide bond between the cysteine residues, as an active substance, along with a pharmaceutically acceptable excipient, wherein said substance is formulated in the form of a sterile injectable solution of oxidized glutathione in a pharmaceutically acceptable solvent, and a pharmaceutically acceptable extender capable of enhancing and prolonging a therapeutic effect of said agent in the body of a user by increasing the half-life of oxidized glutathione, wherein said extender is inosine.

23. A therapeutic agent for treating neoplastic, infectious, hematologic, immunologic and other diseases in which stimulation of the endogenous cytokines and hemopoietic factors production is considered beneficial, said therapeutic agent being in a dosage form for parenteral administration and consisting essentially of an effective amount of oxidized glutathione, a dimer of tripeptide γ-glutamyl-cysteinyl-glycine where two molecules of the tripeptide are linked via covalent disulfide bond between the cysteine residues, as an active substance, along with a pharmaceutically acceptable excipient, wherein said substance is formulated in the form of a sterile injectable solution of oxidized glutathione in a pharmaceutically acceptable solvent, and a pharmaceutically acceptable extender capable of enhancing and prolonging a therapeutic effect of said agent in the body of a user by increasing the half-life of oxidized glutathione, wherein said extender is cystamine.

24. A method of enhancing and prolonging the ability of oxidized glutathione to stimulate endogenous production of cytokine and hemopoietic factor in the body of a user wherein oxidized glutathione is used in a pharmaceutical composition containing pharmaceutically acceptable components said method consisting essentially of obtaining a solution of oxidized glutathione and intermixing therewith an extender, said extender being selected from the group consisting of a donor of reactive oxygen intermediates, hypoxanthine derivatives having the ability to compete with NADP.H to retard GSSG reduction into GSH, a reversible inhibitor of pentose phosphate pathway of glucose oxidation, and mixtures thereof to act as said pharmaceutical composition, and introducing said pharmaceutical composition into the body of a user in an amount effective to cause endogenous production of cytokines and hemopoietic factors.

25. A method in accordance with the method of claim 24, wherein said donor is hydrogen peroxide.

26. A method in accordance with the method of claim 24, wherein said hypoxanthine derivative is inosine.

27. A method in accordance with the method of claim 24, wherein said reversible inhibitor is cystamine.

28. A method of stimulating production of cytokines and hemopoietic factors consisting essentially of introducing in vivo to mammalian cells in need of stimulating production of cytokines or hemopoietic factors or both, an effective amount of oxidized glutathione, for a period of time to stimulate endogenous production of cytokines and hemopoietic factors to obtain a therapeutic effect.

29. A method in accordance with the method of claim 28, wherein said cells are in a mammalian body and said oxidized glutathione is introduced into said body at a rate of from 0.01 to 0.5 mg per kg of body weight, at least one time a day for at least one day.

30. A method in accordance with the method of claim 29, wherein said oxidized glutathione is introduced into said body in an injectable solution form, wherein said oxidized glutathione is present in such solution at a concentration of from 0.01 to 2.0% by weight.

31. A method in accordance with the method of claim 30, wherein said injectable solution comprises an extender selected from the group consisting of hydrogen peroxide, inosine, and cystamine.

32. A method in accordance with the method of claim 28, wherein said cells are in a mammalian body and said oxidized glutathione is introduced topically to a topical area at a dose of from 0.01 to 0.5 mg per meter$^2$ of topical area.

33. A method in accordance with the method of claim 3, wherein said oxidized glutathione is introduced by regional perfusion.

* * * * *